United States Patent [19]

Kashem et al.

[11] Patent Number: 5,374,655
[45] Date of Patent: Dec. 20, 1994

[54] METHODS FOR THE SYNTHESIS OF MONOFUCOSYLATED OLIGOSACCHARIDES TERMINATING IN DI-N-ACETYLLACTOSAMINYL STRUCTURES

[75] Inventors: Mohammed Kashem; Andre P. Venot; Richard Smith, all of Edmonton, Canada

[73] Assignee: Alberta Research Council, Edmonton, Canada

[21] Appl. No.: 914,172

[22] Filed: Jul. 14, 1992

Related U.S. Application Data

[63] Continuation-in-part of Ser. No. 889,017, May 26, 1992, which is a continuation-in-part of Ser. No. 771,259, Oct. 2, 1991, abandoned, which is a continuation-in-part of Ser. No. 714,161, Jun. 10, 1991.

[30] Foreign Application Priority Data

Jun. 10, 1992 [WO] WIPO ............... PCT/CA92/00251

[51] Int. Cl.$^5$ ............... A01N 37/12; A01N 37/44; C07H 15/04; C12N 7/06
[52] U.S. Cl. ............... 514/540; 514/54; 514/567; 514/53; 530/403; 536/116; 536/53; 435/238; 435/193
[58] Field of Search ............... 514/540, 54, 53, 567; 530/403; 536/116, 53; 435/193, 238

[56] References Cited

U.S. PATENT DOCUMENTS

| | | | |
|---|---|---|---|
| 4,137,401 | 1/1979 | Lemieux et al. | 536/116 |
| 4,139,401 | 1/1979 | Lemieux et al. | 536/116 |
| 4,766,150 | 8/1988 | Kiel | 514/567 |
| 5,032,519 | 7/1991 | Paulson et al. | 435/193 |
| 5,059,535 | 10/1991 | Mazid et al. | 435/193 |
| 5,079,353 | 1/1992 | Ratcliffe et al. | 536/53 |
| 5,211,937 | 5/1993 | Brandley et al. | 424/1.1 |

FOREIGN PATENT DOCUMENTS

| | | |
|---|---|---|
| 0319253 | 6/1989 | European Pat. Off. |
| 0395217 | 10/1990 | European Pat. Off. |
| 0410950 | 1/1991 | European Pat. Off. |
| WO92/02527 | 2/1992 | WIPO |

OTHER PUBLICATIONS

Gross et al; Biochem (1989), 28, pp. 7386–7392.
Paulsen, Hans; Agnew Chem. Int. Ed. Engl. 21 (1982) pp. 155–173.
Schaver et al; "Sialic Acids"; 1988; pp. 20–21.
Okamoto et al; Tetrahedron vol. 46, No. 17, pp. 5835–5857 (1990).
Reuter et al; Glycaconjugate J. (1988) 5: pp. 133–135.
Basu et al., Indian J. Biochem. Biophys., 25:112–118 (1988).
Basu et al., J. Biol. Chem., 259:12557–12562 (1984).
Ferenandez–Santana et al., J. Carbohydr. Chem. 8:531–537 (1989).
Foster et al., J. Biol. Chem., 266:3526–3531 (1991).
Fukuda et al., J. Biol. Chem., 261:2376–2383 (1986).
Holmes et al., Arch. Biochem. Biophys., 274:633–647 (1989).
Holmes et al., J. Biol. Chem., 261:3737–3743 (1986).
Holmes et al., J. Biol. Chem. 262:15649–15658 (1987).
Hosomi et al., Japan J. Med. Sci. Biol. 42:77–82 (1989).
Hosomi et al., Jpn. S. Vet. Sci. 51:1–6 (1989).

(List continued on next page.)

Primary Examiner—Jeffrey E. Russel
Assistant Examiner—Louise N. Leary
Attorney, Agent, or Firm—Burns, Doane, Swecker & Mathis

[57] ABSTRACT

Disclosed are methods for the preparation of monofucosylated and sialylated derivatives of the compound βGal(1-4)βGlcNAc(1-3)βGal(1-4)βGlcNAc-OR. In particular, the methods of this invention provide for a multi-step synthesis wherein selective monofucosylation is accomplished on the 3-hydroxy group on only one of the GlcNAc units found in the βGal(1-4) βGlcNAc (1-3) βGal (1-4) βGlcNAc-OR compound. In this step, monofucosylation is achieved by use of the α(1-3)fucosyltransferase.

10 Claims, 8 Drawing Sheets

OTHER PUBLICATIONS

Lee, et al., "Synthesis of 3-(2-Aminoethylthio)propyl Glycosides", Carb. Res., 37: 193-201 (1974).

Lemieux, et al., "The Conformations of Oligosaccharides Related to the ABH and Lewis Human Blood Group Determinants" Can. J. Chem, 58: 631-653 (1979).

Matsumoto, et al., "Derivatization of Epoxy-Activated Agarose with Various Carbohydrates for the Preparation of Stable and High-Capacity Affinity Adsorbents: Their Use For Affinity Chromatography of Carbohydrate-Binding Proteins", Anal. Biochem., 116: 103-110 (1981).

Kukowska-Latallo, et al., "A Cloned Human cDNA Determines Expression of a Mouse Stage-Specific Embryonic Antigen and the Lewis Blood Group $\alpha(1,\frac{1}{3})$ Fucosyltransferase", Genes and Development, 4: 1288-1303 (1990).

Prieels, et al., "Co-Purification of the Lewis Blood Group N-Acetylglucoaminide $\alpha1\rightarrow4$ Fucosyltransferase and an N-Acetylglucosaminide $\alpha1\rightarrow3$ Fucosyltransferase From Human Milk", J. Biol. Chem., 256(20):10456-10463 (1981).

Nunez, et al., "The Synthesis and Characterization of $\alpha$- and $\beta$-L-Fucopyranosyl Phosphates and GDP-Fucose, Can. J. Chem., 59: 2086-2095 (1981).

Schmidt, et al., "Stereospecific Synthesis of $\alpha$- and McEver, "Leukocyte Interactions Mediated by Selectins" Thrombosis and Haemostasis 65(3):223-228 (1991).

Sabesan, et al., "Combined Chemical and Enzymatic Synthesis of Sialyloligosaccharides and Characterization by 500-MHZ $^1$H and $^{13}$C NMR Spectroscopy", J. Am. Chem. Soc., 108:1068-2080 (1986).

Toone, et al., "Enzyme-Catalyzed Synthesis of Carbohydrates" Tetrahedron, 45:5367-5422 (1989).

Palcic, et al., "Enzymatic Synthesis of Oligosaccharides Terminating in the Tumor-Associated Sialyl Lewis-$\alpha$Determinant", Carb. Res., 190:1-11 (1989).

Walz, et al., "Recognition by Elam-1 of the Sialyl-Le$^x$ Determinant on Myeloid and Tumor Cells", Science, 250:1132-1135 (1990).

Tiemeyer, et al., "Carbohydrate Ligands for Endothelial-Leukocyte Adhesion Molecule 1", Proc. Natl. Acad. Sci. (USA), 88:1138-1142 (1991).

Smith, et al., "A Novel Sialylfucopentaose in Human Milk", J. Biol. Chem., 262(25):12040-12047 (1987).

Paulson, et al., "Sialyl-and Fucosyltransferases in the Biosynthesis of Asparaginyl-Linked Oligosaccharides in Glycoproteins", J. Biol. Chem., 253:5617-5624 (1978).

Unverzagt, et al., "High-Efficiecy Synthesis of Sialyloligosaccharides and Sialylglycopeptides", J. Am. Chem. Soc., 112:9308-9309 (1990).

Weinstein, et al., "Purification of a Gal$\beta$ 1$\rightarrow$4GlcNAc$\alpha$2$\rightarrow$6 Sialyltransferase and a Gal $\beta$ 1$\rightarrow$3(4) GlcNAc $\alpha$ 2$\rightarrow$3 Sialyltransferase to Homogeniety from Rat Liver", J. Biol. Chem., 257 (22):13835-13844 (1982).

Paulson, et al., "Purification of Sialytransferase from Bovine Colostrum by Affinity Chromatography on CDP-Agarose", J. Biol. Chem., 252(7) 2356-2362 (1977).

Schmidt, "New Methods for the Synthesis of Glycosides and Oligosaccharides", Agnew. Chem. Int. Ed. Eng., 25:212-235 (1986).

Smith, et al., "Cyclophosphamide and Dimethyl Dioctadecyl Ammonium Bromide Immunopotentiate the Delayed-Type Hypersensitivity Response to Inactivated Enveloped Viruses", Immunology, 58:245-250 (1986).

Sleytr, et al., "Structural and Chemical Characterization of s-Layers of Selected Strains of Baciullus Stearothermophilus and Desulfotomaculum Nigrificatus", Arch. Microbiol., 146:19-24 (1986).

Palcic et al., "Flexibility in the Donor Substrate Specificity of $\beta$-1,4-Galactosyltransferase: Application in the Synthesis of Compexcarbohydrates", Glycobiology 1(2):205-209 (1991).

Palcic et al., "Transfer of D-Galactosyl Groups to 6-O-Substituted 2-Acetamido-2-Deoxy-D-Glucose Residues by Use of Bovine D-Galactosyltransferase", Carb. Res., 159:315-324 (1987).

Wong, et al., "Probing the Acceptor Specificity of $\beta$-1,4-Galactosyltransferase for the Development of Enzymatic Synthesis of Novel Oligosacchardies", J. Am. Chem. Soc., 113: 8137-8143 (1991).

Rana, et al., "Synthesis of Phenyl 2-Acetamido-2-Deoxy-3-O-$\beta$-L-Fucopyranosyl-(3-D-Glucopyranoside and Related Compounds", Carb. Res., 91:149-157 (1981).

Paulsen, et al., Carbohydrate Res., 104:195-219 (1982) (Abstract only).

(List continued on next page.)

OTHER PUBLICATIONS

Hosomi et al., J. Biochem., 95:1655–1659 (1987).
Howard et al., J. Biol. Chem., 262:16830–16837 (1987).
Lowe et al., J. Biol. Chem., 266:17467–17477 (1991).
Lowe et al., Cell, 63:475–485 (1990).
Mollicone et al., Carbohydr. Res., 228:265–276 (1992).
Nilsson et al., J. Carbohydr. Chem., 9:1–19 (1990).
Nudelman et al., J. Biol. Chem., 263:13942–13951 (1988).
Phillips et al., Science, 250:1130–1132 (1990).
Piller et al., J. Biol. Chem., 258:12293–12299 (1983).
Schenkman et al., Cell, 65:1117–1125 (1991).
Takeya et al., Japan J. Med. Sci. Biol. 38:1–8 (1985).
Thiem et al., Angew. Chem. Int. Ed., 30(11):1503–1505 (1991).
Van den Eijnden et al., J. Biol. Chem., 263:12461–12471 (1988).
Van den Eijnden et al., J. Biol. Chem., 258:3435–3437 (1983).
Yates et al., Carbohydr. Res., 120:251–268 (1983).
Zielenski et al., FEBS Lett. 158:164–168 (1983).
Macher, et al., "Human α1—3 Fucosyltransferases" Glycobiology, 1(6):577–584 (1991–Dec.).
Springer, et al., "Sticky Sugars for Selectins", Nature, 349:196–197 (Jan. 1991).
β-L-Fucopyranosyl Phosphates and of GDP-Fucose via Trichloroacetimidate", Liebigs, Ann. Chem., 121–124 (1991).
Veeneman, et al., Tetrahedron Letters, 32: 6175–6178 (1991).

METHODS FOR THE SYNTHESIS OF MONOFUCOSYLATED OLIGOSACCHARIDES TERMINATING IN DI-N-ACETYLLACTOSAMINYL STRUCTURES

CROSS-REFERENCE TO RELATED APPLICATIONS

This application is a continuation-in-part of U.S. Ser. No. 07/889,017 filed May 26, 1992 which, in turn, is a continuation-in-part of U.S. Ser. No. 07/771,259 filed Oct. 2, 1991, now abandoned, which is a continuation-in-part of U.S. Ser. No. 07/714,161 filed Jun. 10, 1991, each of these applications is incorporated herein by reference in its entirety.

BACKGROUND OF THE INVENTION

1. Field of the Invention

This invention is directed to methods for the preparation of monofucosylated and sialylated derivatives of the compound $\beta Gal(1-4)\beta GlcNAc-(1-3)\beta Gal(1-4)\beta GlcNAc$-OR. In particular, the methods of this invention provide for a multi-step synthesis wherein selective monofucosylation is accomplished on the 3-hydroxy group on only one of the GlcNAc units found in the $\beta Gal(1-4)\beta GlcNAc-(1-3)\beta Gal(1-4)\beta GlcNAc$-OR compound. In these methods, monofucosylation is achieved by the use of an $\alpha(1-3)$fucosyltransferase. This invention is also directed to compounds prepared by the herein described methods.

2. References

The following references are cited in this application as superscript numbers at the relevant portion of the application:

1a. Feizi, TIBS, 16:84–86 (1991)
1b. Springer et al., Nature, 349:196–197 (1991)
1c. McEver et al., Thromobosis and Haemostasis, 66:80–87 (1991)
2. Sabesan et al., J. Amer. Chem. Soc., 108:2068–2080 (1986)
3. Toone et al., Tetrahedron 45:5365–5422 (1989)
4. Palcic et al., Carbohydr. Res., 190:1–11 (1989)
5. Walz et al., Science, 250:1132–1135 (1990)
6. Phillips et al., Science, 250:1130–1132 (1990)
7. Tiemeyer et al., Proc. Natl. Acad. Sci. USA, 88:1138–1142 (1991)
8. Holmes et al., J. Biol. Chem., 261:3737–3743 (1986)
8b. Holmes et al., Arch. Biochem. Biophys., 274:633–647 (1989)
8c. Basu et al., Indian J. Biochem. Biophys., 25:112–118 (1988)
8d. Hanisch et al., 178:23–28 (1988)
9. Fukuda et al., J. Biol. Chem., 261:2376–2383 (1986)
10. Nudelman et al., J. Biol. Chem., 263:13942–13951 (1988)
11. Howard et al., J. Biol. Chem., 262:16830–16837 (1987)
12. Johnson et al., Biochem. Soc. Trans. p.396 (1987)
13. Foster et al., J. Biol. Chem., 266:3526–3531 (1991)
14. Smith et al., J. Biol. Chem., 262:12040–12047 (1987)
15. Paulson et al., J. Biol. Chem., 253:5617–5624 (1978)
16. Ichikawa et al., J. Amer. Chem. Soc. 113:4698–4700 (1991)
17. Nilsson et al., J. Carbohydr. Chem., 9:1–19 (1990)
18. Gokhale et al., Can. J. Chem., 68:1063–1071 (1990)
19. Mazid et al., U.S. Pat. No. 5,059,535, Oct. 22, 1991.
20. Weinstein et al., J. Biol. Chem., 257:13835–13844 (1982)
21. Unverzagt et al., J. Amer. Chem. Soc., 112:9308–9309 (1990)
22. Ippolito et al., U.S. patent application Ser. No. 07/714,161 filed Jun. 10, 1991
23. Sialic Acids in "Cell Biology Monographs" Schauer, Editor, 10:6 (1982)
24. Reuter et al., Glycoconjugate J., 5:133–135 (1988)
25. Weinstein et al., J. Biol. Chem., 257:13835–13844 (1982)
26. Paulson et al., J. Biol. Chem., 252:2356–2362 (1977)
27. Paulson, Agnew. Chem. Int. Ed. Eng., 21:155–173 (1982)
28. Schmidt, Agnew. Chem. Int. Ed. Eng., 25:212–235 (1986)
29. Fugedi et al., Glycoconj. J., 4:97–108 (1987)
30. Alais et al., Carbohydr. Res., 207:11–31 (1990)
31. Smith and Ziola, Immunology, 58:245 (1986)
32. Sleytr et al., Arch. Microbiol., 146:19 (1986)
33. Lowe et al., Cell, 63:475–485 (1990)
34. Macher et al. Glycobiology 1(6):577–584 (1991)
35. Lowe et al., J. Biol. Chem., 266:17467–17477 (1991)
36. Piller et al., J. Biol. Chem., 258:12293–12299 (1983)
37. Hosimi et al., Japan J. Med. Sci. Biol. 42:77–82 (1989)
38. Yates et al., Carbohydr. Res., 120:251–268 (1983)
39. Hosomi et al., J. Biochem., 95:1655–1659 (1987)
40. Zielenski et al., FEBS Lett. 158:164–168 (1983)
41. Hosimi et al., Japan J. Med. Sci. Biol. 38:1–8 (1985)
42. Van den Eijnden et al., J. Biol. Chem., 258: 3435–3437 (1983)
43. Van den Eijnden et al., J. Biol. Chem., 263:12461–12471 (1988)
44. Basu et al., J. Biol. Chem., 259:12557–12562 (1984)
45. Hosomi et al., Jpn. S. Vet. Sci. 51:1–6 (1989)
46. Holmes et al., J. Biol. Chem. 262:15649–15658 (1987)
47. Palcic et al., Glycobiology, 1:205–209 (1991)
48. Palcic et al., Carbohydr. Res., 159:315–324 (1987)
49. Wong et al., J. Am. Chem. Soc., 113:8137–8145 (1991)
50. Ekberg et al., Carbohydr. Res. 110:55–67 (1982)
51. Dahmen et al., Carbohydr. Res. 118:292–301 (1983)
52. Rana et al., Carbohydr. Res. 91:149–157 (1981)
53. Amvam-Zollo et al., Carbohydr. Res. 150:199–212 (1986)
54. Paulsen et al., Carbohydr. Res. 104: 195–219 (1982)
55. Chernyak et al., Carbohydr. Res. 128:269–282 (1984)
56. Fernandez-Santana et al., J. Carbohydr. Chem. 8:531–537 (1989)
57. Lee et al., Carbohydr. Res., 37:193 et seq. (1974)
58. Ratcliffe et al., U.S. patent application Ser. No. 07/278,106, filed Nov. 30, 1988
59. Jiang et al., "Chemical Synthesis of GDP-Fucose", U.S. patent application Ser. No. 07/848,223 filed Mar. 9, 1992
60. Weinstein et al., J. Biol. Chem., Vol. 257, No. 22, pp. 13835–13844 (9182)
61. Lemieux et al., Can. J. Chem., 58:631–653 (1980)
62. Ichikawa et al., Anal. Biochem., 202:215–238 (1992)
63. Schenkman et al., Cell, 65:1117–1125 (1991)
64. Thiem et al., Angew. Chem. Int. Ed., 30(11):1503–1505 (1991)
65. Venot et al., U.S. patent application Ser. No. 07/771,259, filed Oct. 2, 1991
66. Lemieux et al., U.S. Pat. No. 4,137,401, Jan. 30, 1979
67. Matsumoto et al., Anal. Biochem., 116 (1981) 103–110

68. Kukowska-Latallo et al., Genes and Development, 4:1288–1303 (1990)
69. Dumas et al., Bioorg. Med. Letters, 1:425–428 (1991)
70. Prieels et al., J. Biol. Chem., 256:10456–10463 (1981)
71. Eppenberger-Castori et al., Glycoconj. J. 6:101–114 (1989)
72. Nunez, et al., Can. J. Chem., 59:2086–2095 (1981)
73. Gokhale et al., Can. J. Chem., 68:1063–1071 (1990)
74. Schmidt, et al., Liebigs Ann. Chem., 121–124 (1991)
75. Veeneman, et al., Tetrahedron Lett., 32:6175–6178 (1991)

All publications and patent applications mentioned in this specification are indicative of the level of skill of those skilled in the art to which this invention pertains. All publications and patent applications are herein incorporated by reference in their entirety to the same extent as if each individual publication or patent application was specifically and individually indicated to be incorporated by reference in its entirety.

3. State of the Art

The art teaches that specific oligosaccharides such as sialylated and fucosylated structures are involved as ligands in cell adhesion phenomena.[1a–1c] Similarly, oligosaccharide glycosides relating to blood group determinant structures have been found to impart immunosuppressive and tolerogenic properties to mammals when the mammals were previously challenged with an antigen. See Ippolito et al.[22], which application is incorporated herein by reference in its entirety. In this regard, oligosaccharide glycosides relating to blood group determinant structures include the compound βGal(1–4)βGlcNAc(1–3)βGal(1–4)βGlcNAc-OR depicted in FIG. 1 of this application as compound 1a.

Ippolito et al.[22] further discloses that blood group determinant oligosaccharide glycosides having a sialic acid group (or an analogue thereof) at the non-reducing sugar terminus of the oligosaccharide glycosides and which are also monofucosylated possess immunosuppressive and tolerogenic properties (e.g., sialyl Lewis$^X$—Compound III in FIG. 12 of Ippolito et al.[22]).

In view of the above, we desired to prepare a monofucosylated derivative of compound 1a having a sialic acid group (or an analogue thereof) at the non-reducing sugar terminus of this compound wherein the fucosyl group was pendant to the 3-hydroxy of only one of the GlcNAc groups.

A synthetic approach employing enzymatic sialylation and fucosylation steps is particularly appropriate in order to provide an efficient route for the preparation of sialylated and monofucosylated derivatives of compound 1a. In this regard, since the work of Sabesan et al.,[2] -sialyltransferases, mostly the βGal(1–4)βGlcNAc α(2–6)- and the βGal(1¾)βGlcNAc α(2–3)-sialytransferases from rat liver and the βGal(1–3)βGalNAc α(2–3)-sialyltransferase from porcine submaxillary gland have often been used for synthetic purposes.[3] The former two sialyltransferases are useful in sialylating a terminal βGal(1–4)βGlcNAc- group in an oligosaccharide glycoside. The latter sialyltransferase which has a wide acceptor specificity, is useful in sialylating a terminal βGal(1–3)βGlcNAc-group in oligosaccharide glycosides based on the Lewis$^c$ (Type I) backbone[4] but, because of the low affinity of this enzyme for the Type II backbone, the synthesis of sialylated N-acetyllactosaminyl structures, such as those present in the sialyl Lewis$^x$,[5] sialyl dimeric Lewis$^{x6}$ or the corresponding internally monofucosylated derivative[7], by use of this sialyltransferase is much more difficult.[4]

By using fucosyltransferases of various specificities, the biosynthetic pathway leading to sialyl Lewis$^x$ and the sialylated dimeric Lewis$^x$ structures has been shown to proceed by the sequential sialylation followed by fucosylation of the Type II precursors.[8a–d] A similar process "extension, sialylation, fucosylation" has also been proposed[9] to lead to internally fucosylated repetitive Type II terminal structures, such as: αNeu5Ac(-2–3)βGal(1–4)βGlcNAc(1–3)βGal(1–4)-[ αFuc(-1–3)]βGlcNAc-.[9] The identification of the new terminal structure βGal(1–4)βGlcNAc(1–3)βGal(1–4)-[[αFuc(-1–3)]βGlcNAc-, defined by the antibody ACFH-18[10], led to a proposed new biosynthetic pathway such as "elongation followed by selective internal fucosylation". While patterns of initial internal monofucosylation of di-N-acetyllactosaminyl glycolipids have been observed for fucosyltransferases present in LEC II Chinese Hamster Ovary mutant[11] and in human colonic adenocarcinoma Colo 205 cells[8b], these fucosyltransferases are not readily available and/or do not selectively lead to monofucosylated structures. Similarly, while fucosyltransferases possessing the specificity required for the synthesis of the internally fucosylated structure αNeu5Ac(2–3)βGal(1–4)GlcNAc-βGal(1–4)[αFuc(-1–3)]GlcNAc have been identified[34] and in one case a recombinant enzyme[35] has been identified, their availability is also limited. Moreover, other α(1–3)fucosyltransferases do not transfer L-fucose onto N-acetylglucosamine moieties found in acceptors possessing a terminal αNeu5Ac(2–3)βGal(1–4)βGlcNAc- sequence.[12,13,34] It has already been noted that "the order of addition of α(1–3) fucose in N-acetyllactosaminyl sequences of glycoconjugates will then depend upon the particular α(1–3)fucosyltransferase present".[11]

The single fucosylation at the internal N-acetylglucosamine unit of the α(2–6)sialyl di-N-acetyllactosaminyl sequence leading to the terminal structure αNeu5Ac(2–6)βGal(1–4)βGlcNAc(1–3)-Gal(1–4)-[αFuc(1–3)]βGlcNAc-[8a] (also proposed for a sialyl-fucopentaose from human milk[14]) is in agreement with the proposed mutually exclusive glycosylation pattern of the βGal(1–4)βGlcNAc α(2–6)sialyltransferase and the βGal(1¾)βGlcNAc α(1¾)fucosyltransferase in the synthesis of asparaginyl linked oligosaccharides in glycoproteins.[15]

In view of the above, processes which would enzymatically prepare sialylated and monofucosylated derivatives of compound 1a without the need to employ a fucosyltransferase specific for monofucosylation would be particularly desirable.

The present invention is based, in part, on the discovery of synthetic pathways which utilizes enzymatic fucosylation and sialylation steps and which result in the selective formation of monofucosylated derivatives of compound 1a without the need to employ a fucosyltransferase which is specific for monofucosylation on either of the GlcNAc units of compound 1a.

SUMMARY OF THE INVENTION

This invention is directed, in part, to the discovery that fucosylation onto the 3-hydroxyl group of the GlcNAc saccharide in a βGal(1–4)βGlcNAc disaccharide via an α(1→3)fucosyltransferase (e.g., βGal(1¾)βGlcNAc α(1¾) fucosyltransferase) is dependent on the presence of a 6-hydroxyl group on the Gal saccharide and when this hydroxyl group is blocked by a removable blocking group, fucosylation on the neighboring GlcNAc group is prevented. In this aspect, the methods of this invention employ this characteristic of α(1-3)fucosyltransferases to provide for a means to selectively monofucosylate compound 1a which are used advantageously to prepare compounds 5a and 12.

In another method aspect, the present invention is directed to the discovery of enzymatic methods and chemical/enzymatic methods to prepare the compound αNeu5Ac(2-3)βGal(1-4)βGlcNAc(1-3)βGal(1-4)-[αFuc(1-3)]βGlcNAc-OR.

Thus, in one of its method aspects, the present invention is directed to a method for preparation of a compound of the formula I:

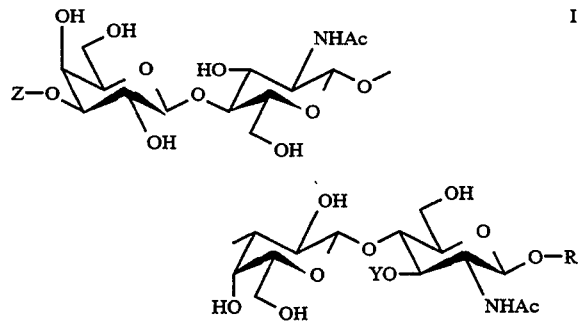

wherein R is hydrogen, a saccharide or an oligosaccharide, or an aglycon group having at least one carbon atom, Y is L-fucose or a compatible analogue of L-fucose, and Z is sialic acid or a compatible analogue of sialic acid, which method comprises the following steps:

(a) preparing a compound of the formula II

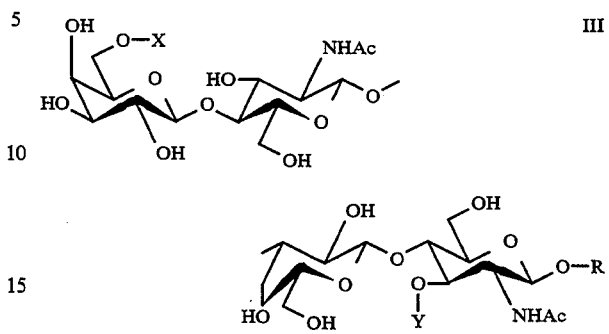

wherein R is as defined above and X is a removable blocking group;

(b) fucosylating the compound prepared in (a) above with an α(1-3)fucosyltransferase so as to form a monofucosylated derivative of the formula III:

wherein X, Y and R are as defined above;

(c) removing the removable blocking group from the compound formed in (b) above; and (d) sialylating the compound formed in (c) above with sialic acid or a compatible analogue of sialic acid using an α(2-3)sialyltransferase so as to form the compound of formula I.

In regard to the above, the sialylation of the oligosaccharide glycoside so as to form an α(2-3)sialyl residue at the non-reducing sugar terminus of the oligosaccharide glycoside is necessarily after removing the blocking group because sialylation with an α(2-3)sialyltransferase requires the presence of a free hydroxyl group at the 6-position of the terminal galactose residue on the oligosaccharide glycoside.

In another of its method aspects, the present invention is directed to a method for preparation of a compound of the formula IV:

wherein R is a hydrogen, a saccharide or an oligosaccharide, or an aglycon group having at least one carbon atom, Y' is L-fucose or a compatible analogue of L-fucose and Z is sialic acid or a compatible analogue of sialic acid, which method comprises the following steps:

(a) preparing a compound of the formula V wherein R is as defined above and X' is a removable blocking group;

(b) sialylating the compound formed in (a) above with sialic acid or a compatible analogue of sialic acid using an α(2-3)sialyltransferase;

(c) fucosylating the compound prepared in (a) above with an α(1-3)fucosyltransferase so as to form a monofucosylated derivative of the formula VI:

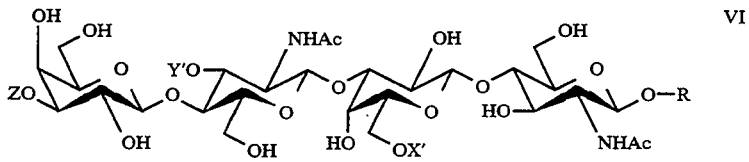

VI wherein X', Y' and R are as defined above; and (d) removing the removable blocking group from the compound formed in (c) above so as to form a compound of formula IV with the proviso that X' is a blocking group other than sialic acid.

In regard to the above, the sialylation of the oligosaccharide glycoside so as to form an α(2-3)sialyl residue at the non-reducing sugar terminus of the oligosaccharide glycoside is necessarily before the fucosylation step because sialylation with an α(2-3)sialyltransferase will not proceed when Y' is L-fucose or a compatible analogue of L-fucose.

Preferred removable blocking groups for use in the above described methods include sialic acid groups and benzyl groups and any other group that can be introduced either enzymatically or chemically on the precursor leading to II or V and later selectively enzymatically or chemically removed in mild conditions compatible with the nature of the product. In compound V, the blocking group X' is not sialic acid because this compound would be difficult to synthesize.

In one of its composition aspects, the present invention is directed to a compound of the formula VII:

carbon atoms with the proviso that when A is a bond then Z' is not hydrogen.

Preferably, the aglycon group is a hydrophobic group. Most preferably, the aglycon moiety is a hydrophobic group selected from the group consisting of —$(CH_2)_8COOCH_3$ and —$(CH_2)_5OCH_2CH=CH_2$ and —$(CH_2)_8CH_2OH$.

The monosialylated and monofucosylated compounds of this invention are particularly useful in modulating a cell-mediated immune inflammatory response. Accordingly, in another of its composition aspects, the present invention is directed to a pharmaceutical composition suitable for administration to a mammal (e.g., human) which comprises a pharmaceutically inert carrier and an effective amount of the compound of Formula I or IV to modulate a cell-mediated immune response in said mammal.

In another of its method aspects, the present invention is directed to a method for modulating a cell-mediated immune response in a mammal which method comprises administering to said mammal an amount of a compound of Formula I or IV effective in modulating said immune response.

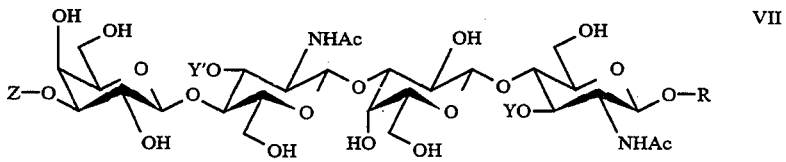

VII wherein R is hydrogen, a saccharide or an oligosaccharide, or an aglycon having at least 1 carbon atom, Y and Y' are selected from the group consisting of hydrogen, L-fucosyl and a compatible analogue of L-fucose with the proviso that one of Y and Y', but not both, is hydrogen, and Z is sialic acid or a compatible analogue of sialic acid.

In a preferred embodiment, the aglycon moiety, R, is selected from the group consisting of —(A)—Z' wherein A represents a bond, an alkylene group of from 2 to 10 carbon atoms, and a moiety of the formula —($CH_2$—$CR_2G$)$_n$— wherein n is an integer equal to 1 to 5; $R_2$ is selected from the group consisting of hydrogen, methyl, or ethyl; and G is selected from the group consisting of hydrogen, halogen, oxygen, sulphur, nitrogen, phenyl and phenyl substituted with 1 to 3 substituents selected from the group consisting of amine, hydroxyl, halo, alkyl of from 1 to 4 carbon atoms and alkoxy of from 1 to 4 carbon atoms; and Z' is selected from the group consisting of hydrogen, methyl, phenyl, nitrophenyl and, when G is not oxygen, sulphur or nitrogen and A is not a bond, then Z' is also selected from the group consisting of —OH, —SH, —$NH_2$, —$NHR_3$, —$N(R_3)_2$, —C(O)OH, —C(O)$OR_3$, —C(O)NH—$NH_2$, —C(O)$NH_2$, —C(O)$NHR_3$, —C(O)N ($R_3$)$_2$, and —$OR_4$ wherein each $R_3$ is independently alkyl of from 1 to 4 carbon atoms and $R_4$ is an alkenyl group of from 3 to 10

BRIEF DESCRIPTION OF THE DRAWINGS

In FIG. 1, the nomenclature for compound 1a is βGal(1-4)βGlcNAc(1-3) βGal(-1-4)βGlcNAc-OR, sometimes called di-N-acetyllactosaminyl tetrasaccharide. Similarly, the hexasaccharide moiety present in compounds 5a and 5b in FIG. 1 is sometimes called VIM-2 epitope or CD-65[5] and 7a and 7b are called sialyl dimeric Lewis[x].

DETAILED DESCRIPTION OF THE INVENTION

Figure 1A:
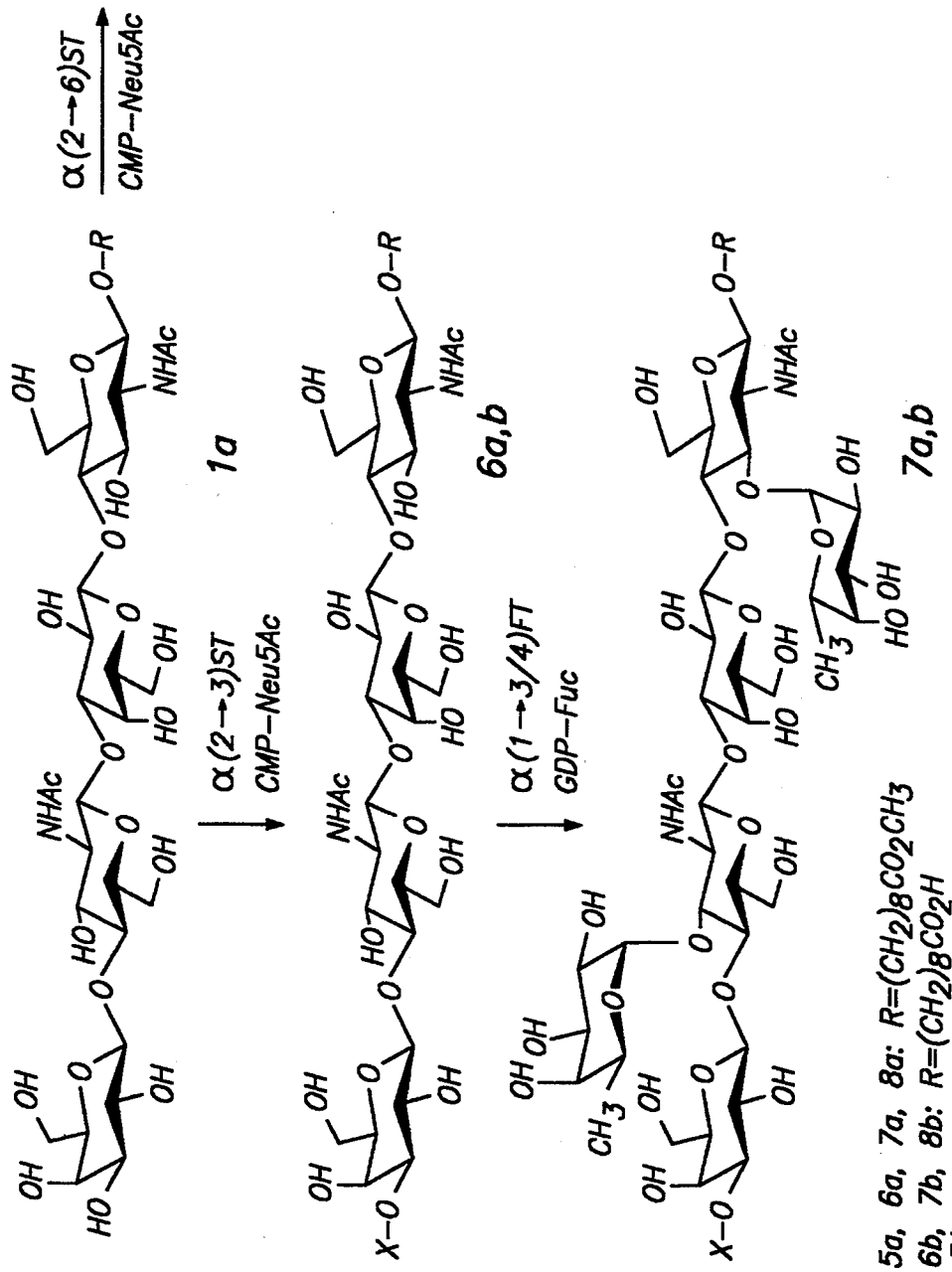
FIG. 1 illustrates the synthetic pathway leading to Sialyl dimeric Lewis[x] and internally monofucosylated derivatives thereof.

The present invention is directed, in part, to the discovery that selective monofucosylation of compound 1a (i.e., βGal(1-4)βGlcNAc(1-3)βGal-(1-4)βGlcNAc-OR), can be achieved by appropriately blocking the 6-hydroxy group on the galactose unit adjacent to GlcNAc unit (in the non-reducing sugar direction) so as to prevent fucosylation of the GlcNAc unit.

The present invention is also directed, in part, to the discovery that the preparation of compounds of Formula I can be achieved by a complete enzymatic process or by a chemo/enzymatic process.

In either case, the synthetic steps employed in the synthesis of the monofucosylated derivatives are critical to produce the monofucosylated derivatives.

The present invention is still further directed to the discovery that the compounds of Formula I and IV are useful for in vivo modulation of a cell mediated immune response in mammals, including humans.

However, prior to discussing this invention in further detail, the following terms will first be defined.

A. Definitions

As used herein, the following terms have the definitions given below:

The term "cell-mediated immune response to an antigen in a mammal" refers to those mammalian immune responses which are mediated by cell-cell interactions. Included within this term are cell mediated inflammatory responses to an antigen such as DTH responses as well as cell-mediated inflammatory responses arising from myocardial infarction, virus-induced pneumonia, shock and sequelae (e.g., multiple organ failure), adult respiratory distress syndrome, psoriasis, arthritis, and the like. Preferably, the cell-mediated immune response is a leucocyte-mediated response.

The term "N-acetyllactosamine" or "LacNAc" refers to the disaccharide βGal(1→4)βGlcNAc which is represented by the formula:

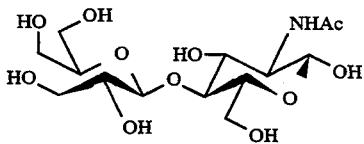

The term "di-N-acetyllactosaminyl structures" means that one N-acetyllactosamine unit is glycosidically linked in a β linkage to the 3-OH of the βGal of the second unit attached to the aglycon.

The term "sialic acid" means all of the naturally occurring structures of sialic acid including (N-acetylated) 5-amino-3,5-dideoxy-D-glycero-D-galacto-nonulopyranosylonic acid ("NeuSAc") and the naturally occurring analogues of Neu5Ac, including N-glycolyl neuraminic acid (Neu5Gc) and 9-O-acetyl neuraminic acid (Neu5,9Ac$_2$), which are compatible with the selected sialyltransferase. A complete list of naturally occurring sialic acids known to date are provided by Schauer[23].

Naturally occurring sialic acids which are recognized by a particular sialyltransferase so as to bind to the enzyme and are then available for transfer to an appropriate acceptor oligosaccharide structure are said to be compatible with the sialyltransferase and are sometimes referred to herein as a "compatible naturally occurring sialic acid".

The term "analogues of sialic acid" refers to analogues of naturally occurring structures of sialic acid including those wherein the sialic acid unit has been chemically modified so as to introduce and/or remove one or more functionalities from such structures. For example, such modification can result in the removal of an —OH functionality, the introduction of an amine functionality, the introduction of a halo functionality, and the like.

Certain analogues of sialic acid are known in the art and include, by way of example, 9-azido-Neu5Ac, 9-amino-Neu5Ac, 9-deoxy-Neu5Ac, 9-fluoro-Neu5Ac, 9-bromo-Neu5Ac, 8-deoxy-Neu5Ac, 8-epi-Neu5Ac, 7-deoxy-Neu5Ac, 7-epi-Neu5Ac, 7,8-bis-epi-Neu5Ac, 4-O-methyl-Neu5Ac, 4-N-acetyl-Neu5Ac, 4,7-dideoxy-Neu5Ac, 4-oxo-Neu5Ac, 3-hydroxy-Neu5Ac, 3-fluoro-Neu5Ac acid as well as the 6-thio analogues of Neu5Ac. The nomenclature employed herein in describing analogues of sialic acid is as set forth by Reuter et al.[24]

Insofar as sialyltransferases are designed to transfer or donate compatible naturally occurring sialic acids, analogues of Neu5Ac are sometimes referred to herein as "artificial donors" whereas the compatible naturally occurring sialic acids are sometimes referred to herein as the "natural donors".

The term "oligosaccharide" as used in conjunction with the R substituent, refers to a carbohydrate structure having from 2 to about 10 saccharide units. The particular saccharide units employed are not critical and include, by way of example, all natural and synthetic derivatives of glucose, galactose, N-acetylglucosamine, N-acetyl-galactosamine, fucose, sialic acid, 3-deoxy-D,L-octulosonic acid, and the like.

In addition to being in their pyranose form, all sugars recited herein are in their D form except for fucose which is in its L form.

The term "sialyltransferase" refers to those enzymes which transfer a compatible naturally occurring sialic acid, activated as its cytidine monophosphate (CMP) derivative, to the terminal galactose group present on natural acceptor structures comprising those terminating in βGal(1-4)βGlcNAc and βGal(1-3)βGlcNAc disaccharides and include enzymes produced from microorganisms genetically modified so as to incorporate and express all or part of the sialyltransferase gene obtained from another source, including mammalian sources.

Such sialyltransferases comprise those that have been identified in the literature as leading to the following structures:

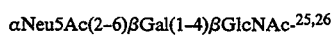

Analogues of sialic acid which are recognized by a particular sialyltransferase so as to bind to the enzyme and are then available for transfer to an appropriate acceptor oligosaccharide structure are said to be compatible with the sialyltransferase and are sometimes referred to herein as a "compatible analogue of sialic acid". Because the transfer reaction employs a sialyltransferase, it goes without saying that an analogue of sialic acid employed in such a reaction must be a compatible analogue of sialic acid.

CMP-nucleotide derivative of Neu5Ac refers to the compound:

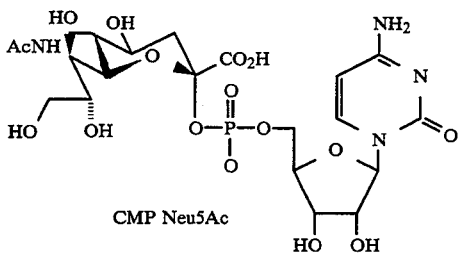

CMP Neu5Ac

CMP-derivatives of analogues of sialic acid refer to those compounds having structures similar to that above with the exception that the Neu5Ac residue is replaced with an analogue of sialic acid.

The term "α(1-3)fucosyltransferase" refers to any fucosyltransferase which transfers L-fucose and compatible analogues of L-fucose from GDP-fucose to the 3 hydroxy position of GlcNAc in a LacNAc group (βGal(1-4)βGlcNAc) in an oligosaccharide glycoside and which does not discriminate between βGal(-1-4)βGlcNAc groups in the oligosaccharide glycoside. The particular α(1-3)fucosyltransferase employed is compatible with the intended reaction. That is to say that the selected α(1-3) fucosyltransferase will bind to the oligosaccharide glycoside employed and transfer L-fucose to the 3 hydroxy position of GlcNAc in a βGal(1-4)βGlcNAc group of the oligosaccharide glycoside. Suitable fucosyltransferases include the known βGal(1→3)βGlcNAc α(1→3)fucosyltransferase which is readily obtained from human milk[4,70,72] and the βGal(1→4)βGlcNAc α(1→3)fucosyltransferase which is also found in human serum and is co-recovered with the βGal(1→3)βGlcNAc α(1→3)fucosyltransferase. A recombinant form of βGal(1→3)βGlcNAc α(1→3)fucosyltransferase is also available[68,69].

Compatible analogues of L-fucose refer to naturally occurring and synthetic analogues of fucose including those where the fucose unit has been chemically modified so as to introduce and/or remove one or more functionalities from this structure. For example, such modification can result in the removal of an —OH functionality, the introduction of an amine functionality, the introduction of a halo functionality, and the like.

Certain compatible analogues of fucose are known in the art and include, by way of example, 3-deoxy-fucose, arabinose, and the like.[18]

The term "removable blocking group" refers to any group which when bound to the 6-hydroxyl of the galactose unit in a βGal(1-4)βGlcNAc group prevents fucosylation of the 3-hydroxyl of the GlcNAc by an α(1-3)fucosyltransferase and which group can be removed by conventional chemical or enzymatic steps to reestablish the 6-hydroxyl on the galactose unit. The particular removable blocking group employed is not critical and preferred removable blocking groups include Neu5Ac and benzyl substituents and any other group that can be introduced either enzymatically or chemically on the precursor leading to II or V and later selectively enzymatically or chemically removed in mild conditions compatible with the nature of the product. One such additional contemplated blocking group is α-galactose which can be removed enzymatically with an α-galactosidase.

The term "removable protecting group" refers to any group which when bound to one or more hydroxyl groups of the galactose, N-acetylglucosamine, etc. which prevent reactions from occurring at these hydroxyl groups and which protecting group can be removed by conventional chemical or enzymatic steps to reestablish the hydroxyl group. The particular removable protecting group employed is not critical and preferred removable hydroxyl protecting groups include conventional substituents such as benzyl, acetyl, chloroacetyl, benzylidine, t-butyl-diphenylsilyl and any other group that can be introduced either enzymatically or chemically onto a hydroxyl functionality and later selectively removed either by enzymatic or chemical methods in mild conditions compatible with the nature of the product. One such additional contemplated protecting group is a α-galactose which can be removed enzymatically with an α-galactosidase.

The term "pharmaceutically acceptable salts" includes the pharmaceutically acceptable addition salts of the compounds of Formula I derived from a variety of organic and inorganic counter salts well known in the art and include, by way of example only, sodium, potassium, calcium, magnesium, ammonium, tetralkylammonium, and the like.

The term "aglycon" refer to the R substituent on the hexasaccharide glycosides of formula I and IV. In general, R is an aglycon having at least 1 carbon atom. In a preferred embodiment, the aglycon moiety, R, is selected from the group consisting of —(A)—Z' wherein A represents a bond, an alkylene group of from 2 to 10 carbon atoms, and a moiety of the formula —(CH$_2$—CR$_2$G)$_n$— wherein n is an integer equal to 1 to 5; R$_2$ is selected from the group consisting of hydrogen, methyl, or ethyl; and G is selected from the group consisting of hydrogen, halogen, oxygen, sulphur, nitrogen, phenyl and phenyl substituted with 1 to 3 substituents selected from the group consisting of amine, hydroxyl, halo, alkyl of from 1 to 4 carbon atoms and alkoxy of from 1 to 4 carbon atoms; and Z' is selected from the group consisting of hydrogen, methyl, phenyl, nitrophenyl, and, when G is not oxygen, sulphur or nitrogen and A is not a bond, then Z' is also selected from the group consisting of —OH, —SH, —NH$_2$, —NHR$_3$, —N(R$_3$)$_2$, —C(O)OH, —C(O)OR$_3$, —C(O)NH—NH$_2$, —C(O)NH$_2$, —C(O)NHR$_3$, —C(O)N(R$_3$)$_2$, and —OR$_4$ wherein each R$_3$ is independently alkyl of from 1 to 4 carbon atoms and R$_4$ is an alkenyl group of from 3 to 10 carbon atoms with the proviso that when A is a bond, Z' is not hydrogen.

In those cases where the aglycon is one which permits linkage of hexasaccharide glycoside I and/or IV to a carrier, then the aglycon is preferably selected from the group consisting of —(A)—Z" wherein A is selected from the group consisting of an alkylene group of from 2 to 10 carbon atoms and a moiety of the form —(CH$_2$—CR$_5$G)$_n$— wherein n is an integer equal to 1 to 5; R$_5$ is selected from the group consisting of hydrogen, methyl, or ethyl; and G is selected from the group consisting of hydrogen, oxygen, sulphur, nitrogen, phenyl and phenyl substituted with 1 to 3 substituents selected from the group consisting of amine, hydroxyl, halo, alkyl of from 1 to 4 carbon atoms and alkoxy of from 1 to 4 carbon atoms; and Z" is selected from the group consisting of hydrogen and, when G is not oxygen, sulphur or nitrogen, then Z" is also selected from the group consisting of —OH, —SH, —NH$_2$, —NHR$_6$, —C(O)OH, —C(O)OR$_6$, —C(O)NHNH$_2$, and —OR$_7$ wherein each R$_6$ is independently alkyl of from 1 to 4 carbon atoms and $R_7$ is an alkenyl group of from 3 to 10 carbon atoms with the proviso that when A is a bond, Z is not hydrogen. In such cases, the —(A)—Z″ group defines a group capable of being linked to a carrier or is capable of being derivatized to a group which is capable of being linked to a carrier. The choice of an appropriate carrier may be useful in enhancing immunogenic properties.

Numerous aglycons are known in the art. For example, a linking arm comprising a para-nitrophenyl group (i.e., —OR=—$OC_6H_4pNO_2$) has been disclosed by Ekberg et al.[50] At the appropriate time during synthesis, the nitro group is reduced to an amino group which can be protected as N-trifluoro-acetamido. Prior to coupling to a support, the trifluoroacetamido group is removed thereby unmasking the amino group.

A linking arm containing sulfur is disclosed by Dahmen et al.[51]. Specifically, the linking arm is derived from a 2-bromoethyl group which, in a substitution reaction with thionucleophiles, has been shown to lead to linking arms possessing a variety of terminal functional groups such as —$OCH_2CH_2SCH_2CO_2CH_3$ and —$OCH_2CH_2SC_6H_4$—$pNH_2$.

Rana et al.[52] discloses a 6-trifluoroacetamidohexyl linking arm (—O—$(CH_2)_6$—$NHCOCF_3$) in which the trifluoroacetamido protecting group can be removed unmasking the primary amino group used for coupling.

Other exemplification of known linking arms include the 7-methoxycarbonyl-3,6,dioxaheptyl linking arm[53] (—$OCH_2$—$CH_2)_2OCH_2CO_2CH_3$; the 2-(4-methoxycarbonylbutancarboxamido)ethyl[54] (—$OCH_2CH_2NHC(O)(CH_2)_4CO_2CH_3$) the allyl linking arm[55] ($OCH_2CH=CH_2$) which, by radical co-polymerization with an appropriate monomer, leads to co-polymers; other allyl linking arms[56] [—$O(CH_2CH_2O)_2CH_2CH=CH_2$]. Additionally, allyl linking arms can be derivatized in the presence of 2-aminoethanethiol[57] to provide for a linking arm —$OCH_2CH_2CH_2SCH_2CH_2NH_2$.

Additionally, as shown by Ratcliffe et al.[58], R group can be an additional saccharide or an oligosaccharide containing a linking arm at the reducing sugar terminus.

The carrier is generally a small molecular weight, non-immunogenic or antigenic carrier including the linking to a fluorescent label, a radioactive label, biotin, or a photolabile linking arm or a moiety to be targeted.

In either case, the aglycon moiety is preferably a hydrophobic group and more preferably a hydrophobic moiety selected from the group consisting of —$(CH_2)_8COOCH_3$ and —$(CH_2)_5OCH_2CH=CH_2$. In particular, the use of a hydrophobic group and most especially, a —$(CH_2)_8COOCH_3$ or —$(CH_2)_5OCH_2CH=CH_2$ group may provide for some enhancement in the kinetics of sialic acid transfer via a sialyltransferase.

As is apparent, hexasaccharide glycosides I and IV described above are different from oligosaccharides and glycoconjugates because the aglycon moiety (R) is not hydrogen, a protein, or a lipid capable of forming a micelle or other large aggregate structure.

B. SYNTHESIS AND METHODOLOGY

B1. Preparation of Starting Materials

Tetrasaccharide glycosides II and V are readily prepared either by complete chemical synthesis or a chemical/enzymatic synthesis as described below. Specifically, tetrasaccharide glycoside II and V can be prepared by chemically coupling the individual saccharide units. Such coupling can readily be prepared using a convergent synthesis, i.e., appropriate saccharide units are linked together to form two disaccharides which are then linked together to form a tetrasaccharide. Alternatively, the synthesis of tetrasaccharide glycosides can be conducted in a sequential synthesis starting with the saccharide unit at the reducing sugar terminus and sequentially adding another saccharide unit until tetrasaccharide glycosides II and V are prepared.

In either case, the first step of the synthesis involves the addition of the aglycon moiety at the anomeric carbon atom of the reducing sugar unit. This is generally accomplished by using an appropriately protected form of the reducing sugar and then selectively modifying this sugar at its anomeric center so as to introduce a leaving group comprising halides, trichloroacetimidate, thioglycoside, etc. The sugar donor is then reacted under catalytic conditions (e.g., a soluble silver salt such as silver trifluoromethanesulfonate, a Lewis acid such as boron trifluoride etherate or trimethylsilyltrifluoromethanesulfonate, or thioglycoside promoters such as methyl trifluoromethanesulfonate or dimethyl(-methylthio)-sulfonium trifluoromethanesulfonate) with an aglycon or an appropriate form of a carbohydrate acceptor which possess one free hydroxyl group at the position where the glycosidic linkage is to be established. See, for example, Paulsen[27], Schmidt[28], and Fügedi et al.[29], the disclosures of each of these references are incorporated herein by reference in their entirety. A large variety of aglycon moieties are known in the art and can be attached with the proper configuration to the anomeric center of the reducing unit.

Appropriate use of compatible protecting groups, well known in the art of carbohydrate synthesis, will allow the further attachment of the other saccharide units. Each of the steps required to form tetrasaccharide glycosides II and V is well known in the art. For example, the synthesis of compound 1a (FIG. 1), i.e., the synthesis of a protected form of a N-acetyllactosaminyl glycoside acceptor and its glycosidation by an appropriate form of a N-acetyllactosaminyl donor are well known in the art[30].

The synthesis of saccharide precursors having removable blocking group(s) is well known in the art and the removable blocking group can be introduced at an appropriate stage during synthesis of tetrasaccharides II or V. For example, the selective opening of a 4',6'—O—benzylidene of a glycoside and/or a thioglycoside of an appropriate form of a lactosamine disaccharide will provide the corresponding 6'—O—benzyl derivative. The protected form of the 6'—O—benzyl thioglycoside will be used as a donor in a glycosidation reaction leading to compound II, after deprotection. The appropriate form of the 6'-O-benzyl lactosaminyl glycoside will be used as acceptor in a glycosidation reaction leading to tetrasaccharide V after deprotection.

When the removable blocking group is sialic acid, then this group can be readily introduced into tetrasaccharide VIII

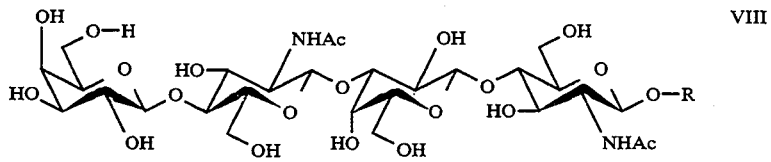

or into disaccharide IX

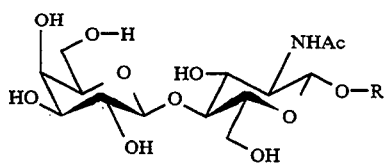

by use of a α(2–6)sialyltransferase as described below.

B2. Enzymatic Sialylation

As noted above, deblocked (i.e., the removable blocking group X or X' is removed) pentasaccharide glycoside III or blocked tetrasaccharide glycoside V ("oligosaccharide glycoside") is sialylated by contacting the appropriate oligosaccharide glycoside with an α(2–3)sialyltransferase and a compatible CMP-derivative of a sialic acid or an analogue thereof under conditions wherein the sialic acid or the compatible analogue thereof is transferred to the non-reducing sugar terminus of the oligosaccharide glycoside. Suitable conditions, known in the art, include the addition of the appropriate sialyltransferase to a mixture of the oligosaccharide glycoside and of the CMP-derivative of the sialic acid in an appropriate buffer such as 0.1 M sodium cacodylate in appropriate conditions of pH and temperature such as at a pH of 6.5 to 7.5 and a temperature between 25° and 45° C., preferably 35°–40° C. for 12 hours to 4 days. The resulting sialylated oligosaccharide glycoside can be isolated and purified using conventional methodology comprising HPLC, gel-, reverse phase-, ion exchange-, or adsorption chromatography.

In this regard, when a compatible analogue of sialic acid is transferred to the oligosaccharide glycoside by the sialyltransferase, the analogue is sometimes referred to as an artificial donor and the oligosaccharide glycoside is sometimes referred to as an artificial acceptor. Sialylation methods employing an artificial donor and an artificial acceptor are described by Venot et al., U.S. patent application Ser. No. 07/771,007 filed Oct. 2, 1992 which application is incorporated herein by reference in its entirety. Similarly, sialylation methods employing an artificial donor and an artificial acceptor are described by Ippolito et al.,[22] which application is also incorporated herein by reference in its entirety.

The enzymatic transfer of compatible analogues of sialic acid require the prior synthesis (i.e., activation) of their nucleotide (CMP) derivatives. Activation of the analogues of sialic acid is usually done by using the enzyme CMP-sialic acid synthase which is readily available and the literature provides examples of the activation of various analogues of sialic acid.

Figure 1B:
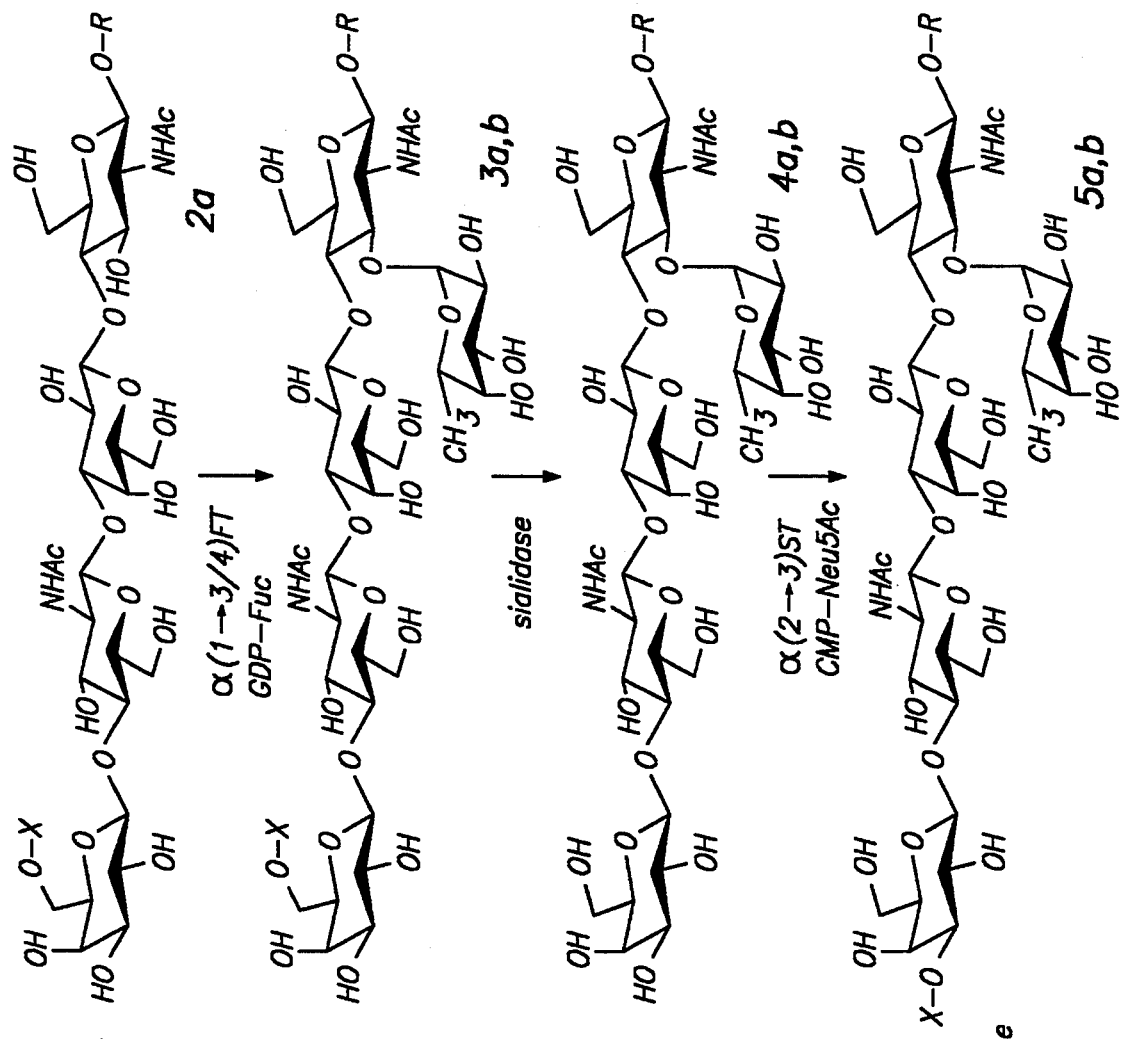

The present invention is based, in part, on the discovery that, as shown in FIG. 1, sialylation of deblocked pentasaccharide glycoside III so as to form an α(2–3)-sialyl residue at the non-reducing sugar terminus of this oligosaccharide glycoside is necessarily after removing the removable blocking group because sialylation with an α(2–3)sialyltransferase requires the presence of a free hydroxyl group at the 6-position of the terminal galactose residue on the deprotected pentasaccharide glycoside III.

Figure 2:
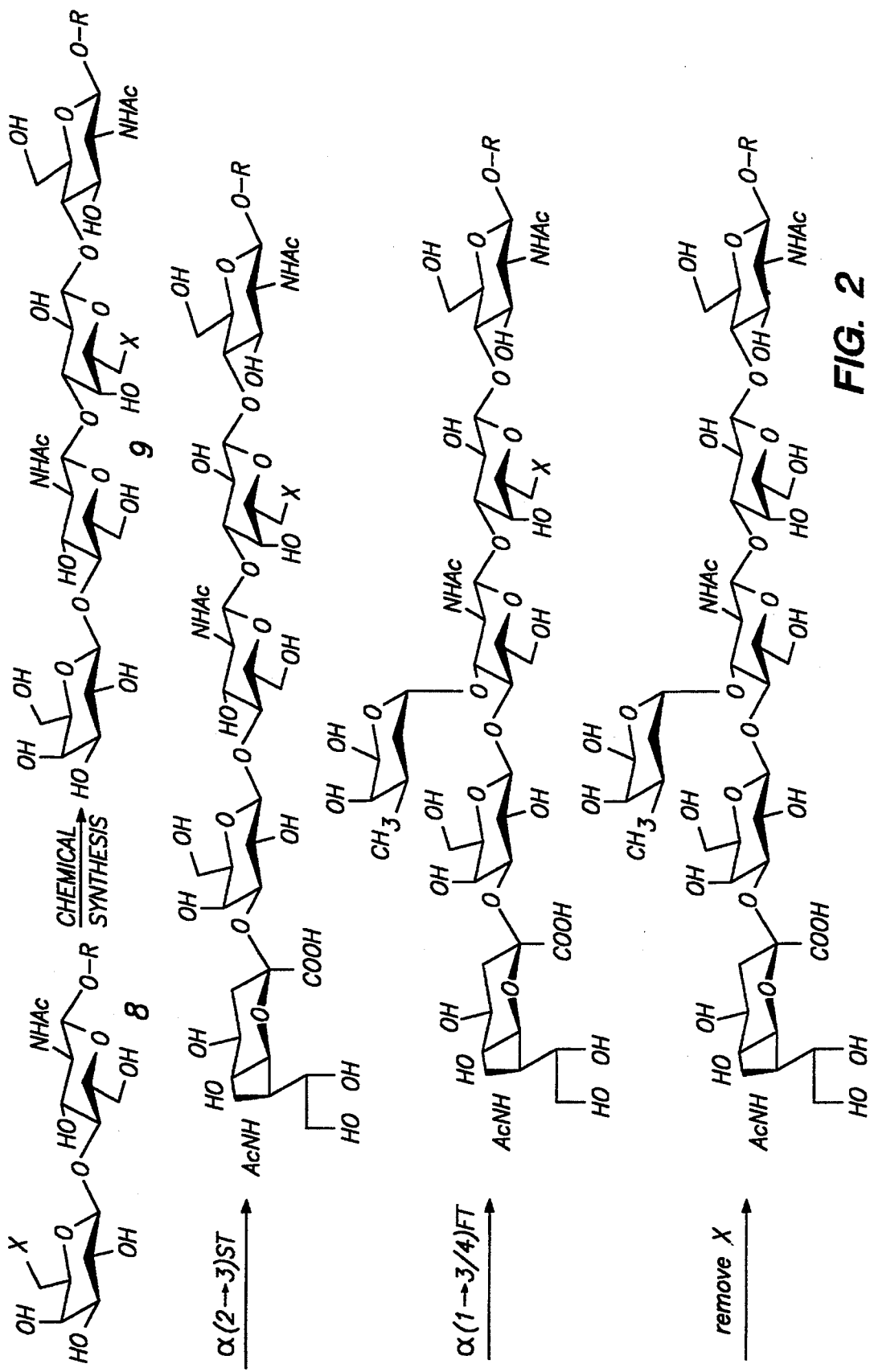
FIG. 2 illustrates the synthetic pathway leading to the externally monofucosylated derivatives of the sialyl di-N-acetyllactosaminyl hapten.

This invention is based, in part, on the further discovery that, as shown in FIGS. 2, the sialylation of the tetrasaccharide glycoside V so as to form an α(2–3)sialyl residue at the non-reducing sugar terminus of this oligosaccharide glycoside is necessarily before the fucosylation step because sialylation with an α(2–3)sialyltransferase will not proceed if there is an α-fucose linked (1–3) to the neighboring N-acetylglucosamine.

B3. Enzymatic Fucosylation

As noted above, tetrasaccharide glycoside II or pentasaccharide glycoside derived by sialylating tetrasaccharide glycoside V or trisaccharide 19 ("oligosaccharide glycoside") are fucosylated by contacting the appropriate oligosaccharide glycoside with an α(1–3)-fucosyltransferase and a compatible GDP-derivative of L-fucose or an analogue of L-fucose under conditions wherein the fucose is transferred onto the 3-hydroxy group of one of the GlcNAc moieties of the oligosaccharide glycoside. Suitable conditions, known in the art, include the addition of the α(1–3)fucosyltransferase to a mixture of the oligosaccharide glycoside and of the GDP-derivative of the L-fucose or compatible analogue thereof in a appropriate buffer such as 0.1 M sodium cacodylate in appropriate conditions of pH and temperature such as at a pH of 6.5 to 7.5 and a temperature between 25° and 45° C., preferably 35° to 40° C. for 12 hours to 4 days. The resulting fucosylated oligosaccharide glycoside can be isolated and purified using conventional methodology comprising HPLC, gel-, reverse phase-, ion exchange-, or adsorption chromatography.

As noted above, enzymatic fucosylation requires the prior synthesis of GDP-fucose. Preferably, GDP-fucose is prepared in the methods described by Jiang et al.[59]

B4. Removal of the Removable Blocking Group

The synthesis of both hexasaccharides I and IV, as per FIGS. 1–2, both require the removal of a removable blocking group. In general, the appropriate oligosaccharide glycoside is treated under conditions sufficient to effect removal of the blocking group. The specific conditions depend on the blocking group employed and are well known in the art. For example, when a benzyl blocking group is employed, this group is readily removed by hydrogenation techniques known in the art. Similarly, when the blocking group is sialic acid, it is removed in the manner depicted in the Examples set forth herein below.

Regarding FIGS. 1–2, FIG. 1 illustrates the synthesis of hexasaccharide glycoside I (compound 5a and 5b) and heptasaccharide glycoside (compound 7a and 7b). Thus, the tetrasaccharide 1a was transformed into 2a by using the βGal(1–4)βGlcNAc α(2–6) sialyltransferase from rat liver (FIG. 1). It has been shown that a similar synthesis can be achieved on gram scale.[16] Pentasaccharide 2a was then selectively fucosylated by the βGal(-

1-3)βGlcNAc α(1¾)fucosyltransferase [α(1¾)FT] from human milk[4] giving the hexasaccharides 3a,b Quantitative desialylation of 3a,b by a suitable immobilized sialidase (e.g., a sialidase from Clostridium Perfringens) led to the fucosylated derivatives 4a,b, the $^1$H-n.m.r. of which were in agreement with that of a synthetic material.[17] The free acid form 4b could be transformed into the methyl ester 4a by action of diazomethane in methanol. Desialylation of a glycolipid possessing of the same terminal hexasaccharide sequence has already been mentioned[10]. Finally, sialylation of 4a by the βGal(1¾)βGlcNAc α(2-3)sialyltransferase from rat liver provided the hexasaccharides 5a,b.

The 8-methoxycarbonyloctyl glycoside of the starting tetrasaccharide 1a and trisaccharide 9 was used with the intention of taking advantage of the hydrophobic properties of the aglycone for separation purposes and with the aim of possible coupling of the products to carriers.[4] In fact, partial hydrolysis of the methyl ester could not really be avoided, and this side reaction became important in some cases (e.g., when the transferase such as milk fucosyltransferase was not highly purified). As a result, compounds 3a, 4a, 5a, 6a and 7a were isolated as the methyl ester and/or the free acid forms (3b, 4b, 5b, 7b) of the aglycone which were identified by $^1$H-n.m.r. However, the free acid form of 4b can readily be reconverted back to the methyl ester by treating the acid in dry methanol with diazomethane.

Finally, although conversion of 1a into 2a appeared almost complete, some losses occurred during recovery of this derivative as it is not very tightly retained on the hydrophobic C18 silica gel.

FIG. 1 also illustrates that heptasaccharide 7b was obtained by sequential sialylation of 1a by the βGal(1¾)βGlcNAc α(2-3)sialyltransferase, followed by difucosylation of the intermediate 6a by the βGal(1¾)βGlcNAc α(1¾)fucosyltransferase from human milk. In the conditions used, only the difucosylated product was obtained.

FIG. 2 illustrates the synthesis of hexasaccharide IV (compound 12).

Figure 3:
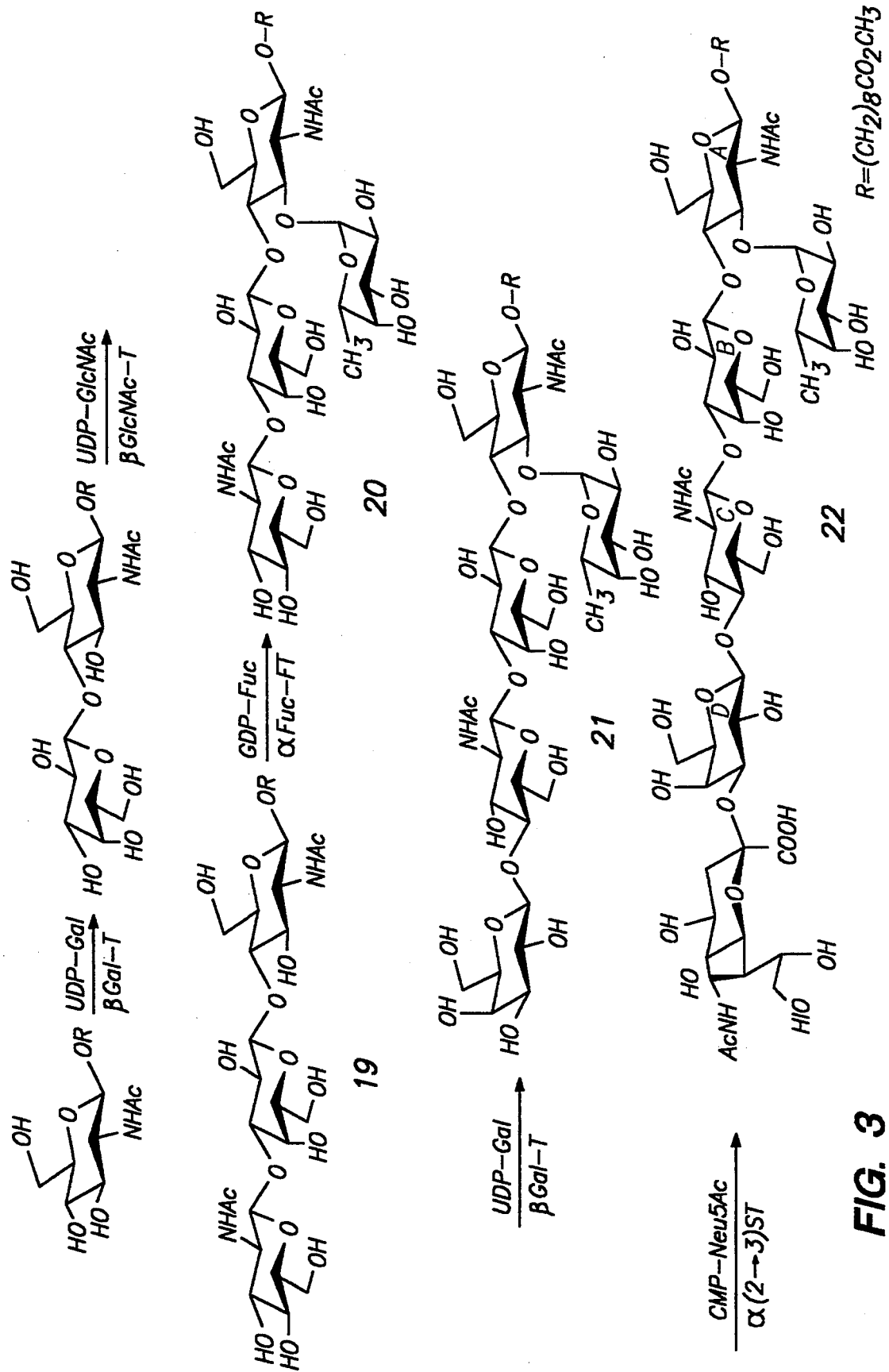
FIG. 3 illustrates an enzymatic pathway leading to monofucosylated and monosialylated compounds of Formula I.

Alternative syntheses for hexasaccharide I are set forth below and generally involve a chemical/enzymatic approach. One approach is a totally enzymatic method which utilizes different glycosyltransferases. This procedure is set forth in FIG. 3. Specifically, in this approach, galactose is enzymatically transferred onto GlcNAc-OR to form βGal(1-4)βGlcNAc-OR (LacNAc-OR). Suitable enzymes include the GlcNAc β1-4 galactosyltransferase which transfers galactose from uridine 5' (galactopyranosyl)-diphosphate (UDP-Gal) to the 4-position of GlcNAcβ-OR, where R can be an aglycone or a saccharide. This transferase is a commercial and versatile enzyme and accepts some modifications in the sugar portion of the donor[47] and in the acceptor[48-49].

N-acetylglucosamine is then transferred to the 3-position of the terminal β-galactose of LacNAc-OR (N-acetyllactosamine-OR—βGal(1-4)βGlcNAc-OR) to produce the βGlcNAc(1-3)βGal(1-4)βGlcNAc-OR trisaccharide structure (compound 19). Transferases which transfer N-acetylglucosamine from uridine 5'-(N-acetylglucosamine)-diphosphate (UDP-GlcNAc) to the 3 position of the terminal β-galactose of a N-acetyllactosamine moiety) are present in a variety of sources such as human serum[36-40], human urine[41], Novikoff tumor cell ascites fluid[42,43], mouse T-lymphoma cells[44], human milk[45] and human colonic adenocarcinoma cells[46].

The acceptor specificity of the transferases obtained, particularly from human serum[36,38] and from Novikoff tumor cell ascites fluid[43], has been well characterized using synthetic oligosaccharides. This enzyme requires a terminal βGal(1-4)βGlc(NAc)-OR unit, where R can be an aglycone or a saccharide moiety and Glc(NAc) can be either GlcNAc or Glc. The enzyme does not transfer to the structure βGal(1-4)[αFuc(1-3)]βGlcNAc (Lewis$^x$) in which the fucose is attached to the penultimate GlcNAc[36,43]. As a result, in this process, enzymatic formation of the βGlcNAc(1-3)βGal(-1-4)βGlcNAc-OR should precede fucosylation. In addition, this enzyme, in combination with the GlcNAc β(1-4) galactosyl-transferase could catalyze the synthesis of oligomers of N-acetyllactosamine[43].

Enzymatic transfer of fucose to the acceptor 19 by the milk Gal(1¾)GlcNAc α(1¾)fucosyl-transferase specifically occurs on the internal GlcNAc leading to compound 20. The backbone of the tetrasaccharide 20 is then extended by transfer of a galactose residue leading to compound 21 by the bovine GlcNAc β1-4 galactosyltransferase. NeuSAc is then transferred to compound 21 (also shown in FIG. 1 as compounds 4a,b) in the last step by the rat liver Gal(β1¾)GlcNAc α2-3 sialyltransferase[60] providing hexasaccharide 22 (also shown in FIG. 1 as compounds 5a,b).

As a result, the last three steps of this synthetic pathway, (1) fucosylation, (2) extension and (3) sialylation, differ from the proposed normal biosynthetic pathway which sequentially proceeds following the sequence: (1) extension, (2) sialylation, and finally (3) fucosylation.

Figure 4A:
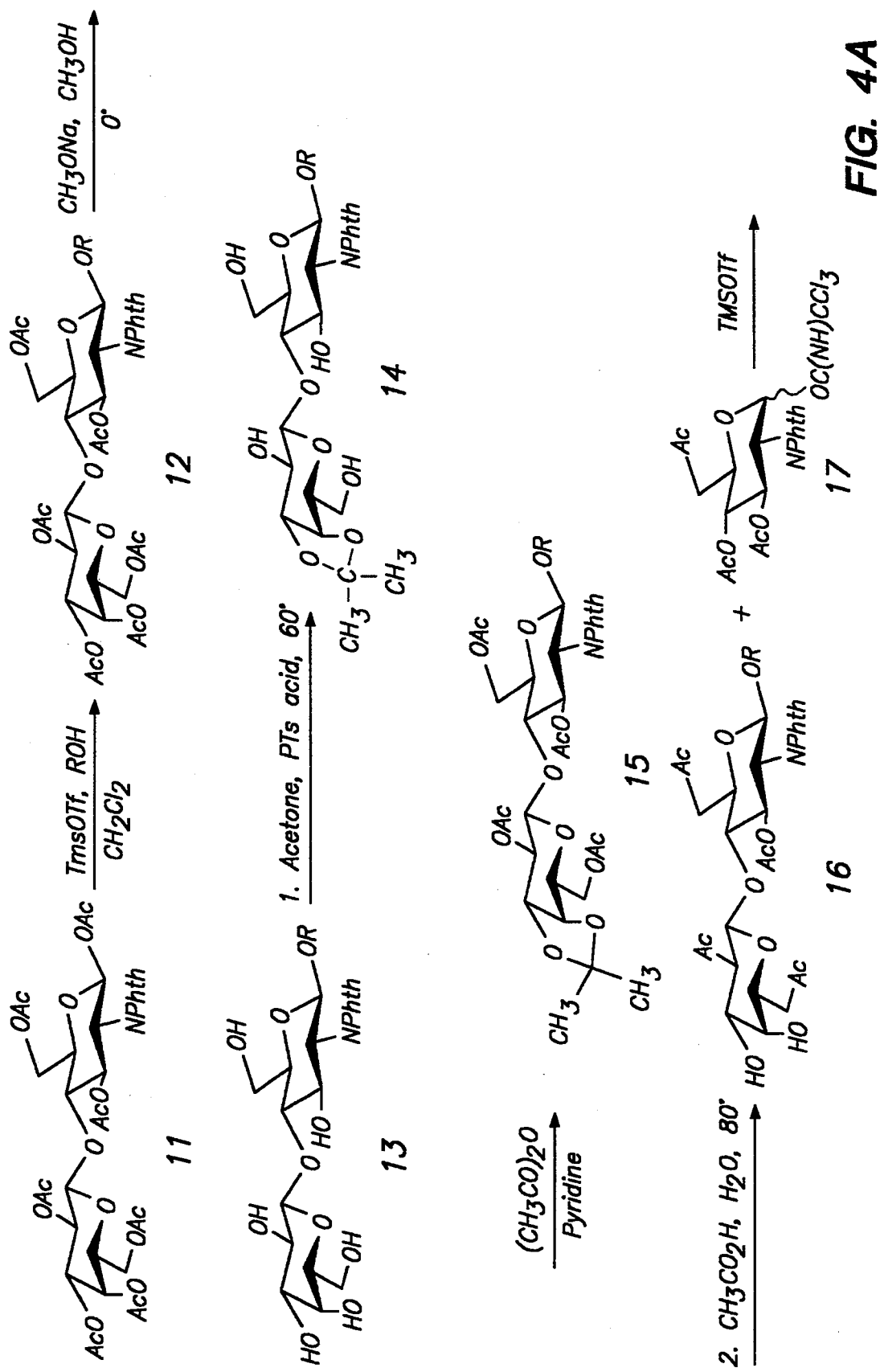
FIG. 4 illustrates an alternative chemical synthesis of trisaccharide 19 which can then be used as per FIG. 3 to prepare monofucosylated and monosialylated compounds of Formula I.
Figure 4B:
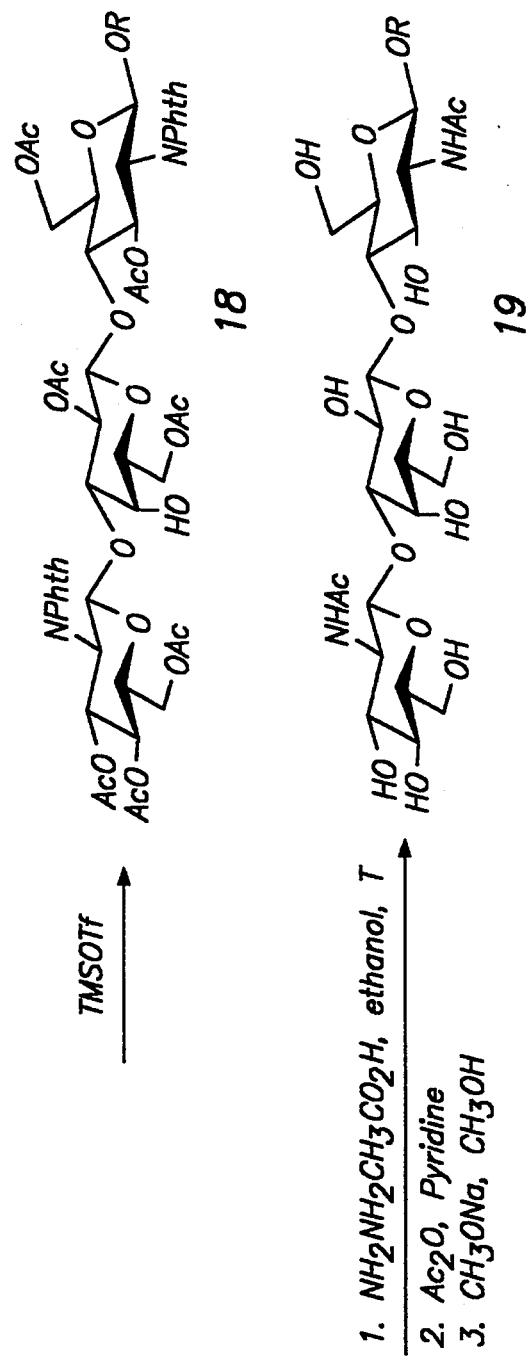

Alternatively, as shown in FIG. 4, compound 19 can be made in a totally synthetic scheme starting from known precursors. Specifically, compound 19 can be obtained by total chemical synthesis following known procedures by which a large variety of R group can be introduced. As a result, R can be an aglycone or a saccharide moiety itself attached to an aglycone. A wide variety of glycosylation methods are available in order to synthesize β-glycosides. The present synthesis is derived from the synthesis described by Alais et al.[30].

In addition, glycosidases can be used, instead of glycosyltransferases, for the synthesis of glycosides in appropriate conditions. The main characteristics of the use of both types of enzymes have been reviewed by Ichikawa et al.[62]. The β-galactosidases, N-acetylhexsaminidase or sialidases[63,64] could be used to synthesize some of the saccharides.

In these synthesis, the 2-N-phthalimido protecting group is used in order to preferably lead to the β-glycosides during glycosylation reactions. Thus the blocked disaccharide glycosyl donor 11[30] is used in a glycosylation reaction of the desired alcohol ROH catalyzed by trimethylsilyltrifluoromethanesulfonate to lead to the glycoside 12. Mild de—O—acetylation provided 13. Disaccharide 13 is reacted with acetone in the presence of an acid catalyst, such as p-toluene sulfonic acid at 60° C., leading to a mixture of the 3,4- and of the 4,6-isopropylidene derivative 14 and 15 which are separated. The 3,4-isopropylidene derivative 14 is totally acetylated in pyridine with acetic anhydride and the isopropylidene group hydrolyzed in a mixture of acetic acid and water at 90° C. providing Glycosylation of diol 16 by the donor 17 catalyzed by trimethylsilyltrifluoromethanesulfonate preferably led to trisaccharide 18 which was deprotected using conventional procedures leading to 19.

As set forth above, L-fucose is then transferred from GDP-fucose to the trisaccharide acceptor 19 by using the Gal($\beta$1¾)GlcNAc $\alpha$1¾ fucosyltransferase from human milk. Another appropriate transferase from other source can also be used. As evidenced by $^1$H-n.m.r., only one fucosyl unit is introduced. Furthermore, the $^1$H-n.m.r. data, in particular the position of the signal provided by H-5 of the $\alpha$Fuc is characteristic of the presence of the Gal($\beta$1–4)[Fuc($\alpha$1–3)]GlcNAc unit[61]. The transformation is quantitative.

Galactose is then transferred from UDP-Gal to tetrasaccharide 20 by the commercial bovine milk GlcNAc $\beta$1–4 galactosyltransferase. The pentasaccharide obtained is identical to the same compound obtained earlier by using a different route[65]. The transformation is quantitative.

In a final step, Neu5Ac is transferred to pentasaccharide 21 by using the Gal($\beta$1¾)GlcNAc $\alpha$(2–3)sialyltransferase from rat liver[25]. Another appropriate transferase from other sources can also be used. This step is performed according to the earlier report and provides the same product as described in Venot et al.[65].

Figure 5A:
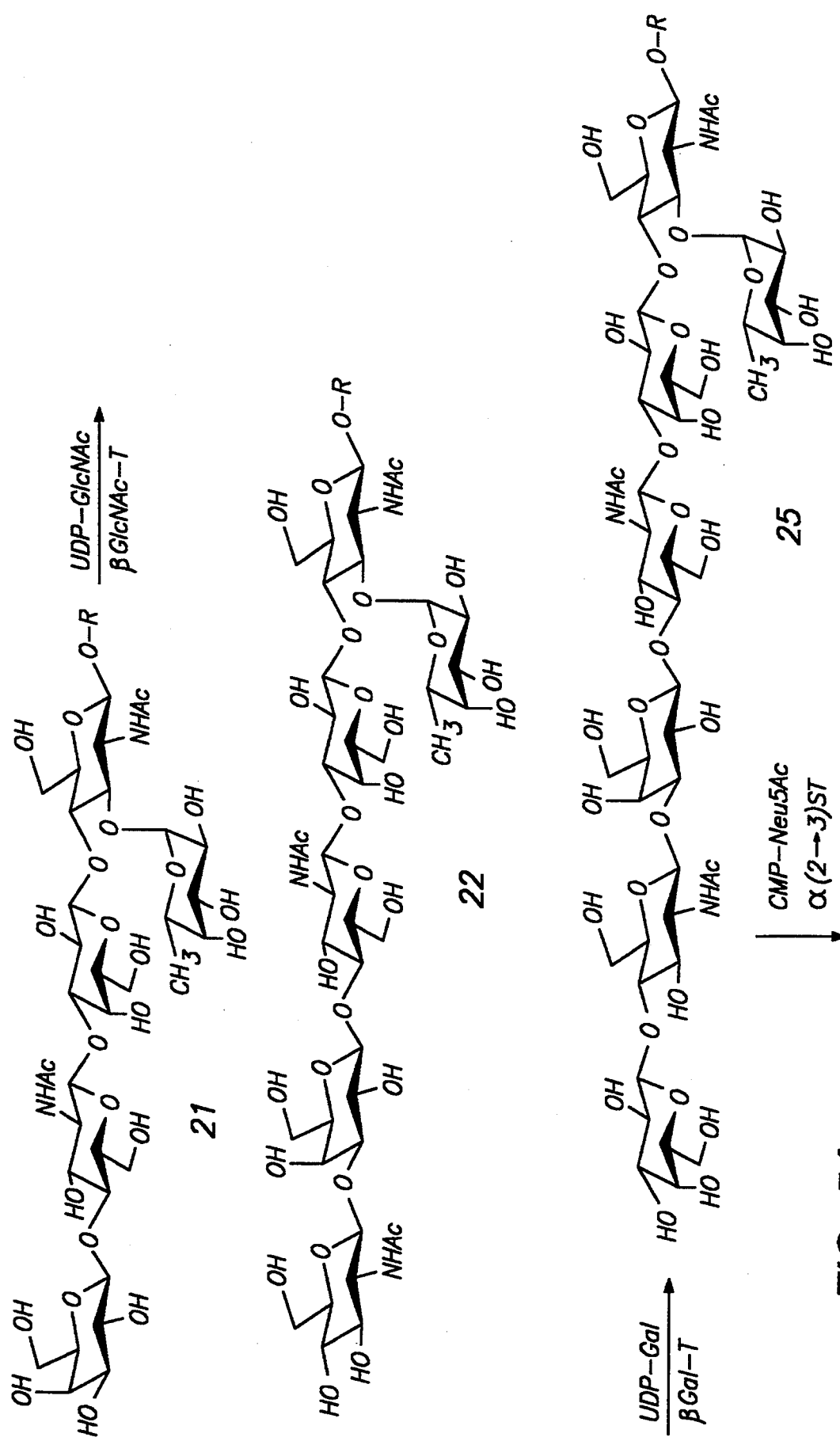
FIG. 5 illustrates that the enzymatic pathway set forth in FIG. 3 can be used to extend the structure of the hexasaccharides of Formula I.
Figure 5B:
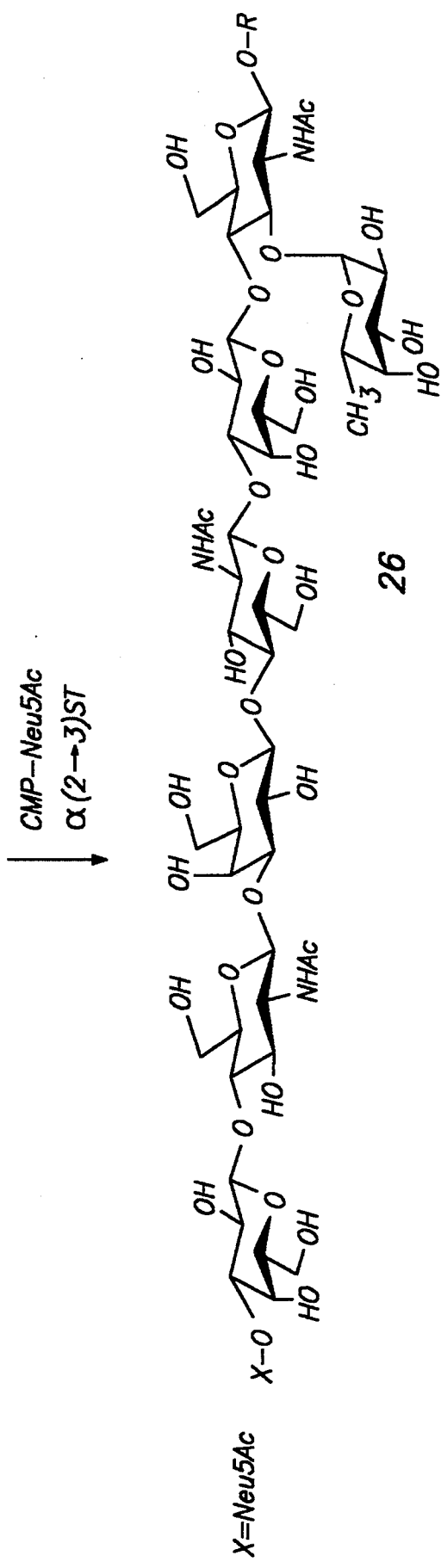

As is apparent, more extended structures can be obtained from the pentasaccharide 21 as indicated in FIG. 5. For that purpose, GlcNAc can be transferred to pentasaccharide 21 by the Gal($\beta$1–4)GlcNAc $\beta$1–3 N-acetylglucosaminyltransferase. Pentasaccharide 21 should be an acceptor for this transferase since the $\alpha$-fucosyl residue is not linked to the penultimate GlcNAc moiety. Further sequential transfer of galactose and of Neu5Ac by the appropriate glycosyltransferase will lead to octasaccharides 26.

C. Utility

Hexasaccharide glycosides I and IV are effective in suppressing mammalian cell-mediated immune responses. Without being limited to any theory, it is believed that these compounds affect the cell mediated immune response in a number of ways. Specifically, these compounds can inhibit the ability of the immune response to become educated about a specific antigen when the compound is administered simultaneously with the first exposure of the immune system to the antigen. Also, hexasaccharide glycosides I and IV can inhibit the effector phase of a cell-mediated immune response (e.g., the inflammatory component of a DTH response) when administered after second or later exposures of the immune system to the same antigen. Additionally, hexasaccharide glycosides I and IV can induce tolerance to antigens when administered at the time of second or later exposures of the immune system to the antigen.

The suppression of the inflammatory component of the immune response by hexasaccharide glycosides I and IV is believed to require the initiation of a secondary immune response (i.e., a response to a second exposure to antigen). Hexasaccharide glycoside I or IV is generally administered to the patient at least about 0.5 hours after an inflammatory episode, preferably, at least about 1 hour after, and most preferably, at least about 5 hours after an inflammatory episode or exacerbation.

Hexasaccharide glycosides I and IV are effective in suppressing cell-mediated immune responses to an antigen (e.g., the inflammatory component of a DTH response) when administered at a dosage range of from about 0.5 mg to about 50 mg/kg of body weight, and preferably from about 0.5 to about 5 mg/kg of body weight. The specific dose employed is regulated by the particular cell-mediated immune response being treated as well as by the judgment of the attending clinician depending upon factors such as the severity of the adverse immune response, the age and general condition of the patient, and the like. Hexasaccharide glycosides I or IV is generally administered parenterally, such as intranasally, intrapulmonarily, transdermally and intravenously, although other forms of administration are contemplated. Preferably, the suppression of a cell-mediated immune response, e.g., the inflammatory component of a DTH response, is reduced by at least about 10% as opposed to control measured 24 hours after administration of the challenge to the mammal and 19 hours after administration of hexasaccharide glycosides I or IV.

In addition to providing suppression of the inflammatory component of the cell-mediated immune response to an antigen, administration of the hexasaccharide glycosides I or IV also imparts a tolerance to additional challenges from the same antigen. In this regard, rechallenge by the same antigen weeks after administration of hexasaccharide glycosides I or IV results in a significantly reduced immune response.

Administration of hexasaccharide glycosides I or IV simultaneously with first exposure to an antigen imparts suppression of a cell-mediated immune response to the antigen and tolerance to future challenges with that antigen. In this regard, the term "reducing sensitization" means that the hexasaccharide glycosides I or IV, when administered to a mammal in an effective amount along with a sufficient amount of antigen to induce an immune response, reduces the ability of the immune system of the mammal to become educated and thus sensitized to the antigen administered at the same time as hexasaccharide glycosides I or IV. An "effective amount" of this compound is that amount which will reduce sensitization (immunological education) of a mammal, including humans, to an antigen administered simultaneously as determined by a reduction in a cell-mediated response to the antigen such as DTH responses as tested by the footpad challenge test. Preferably the reduction in sensitization will be at least about 20% and more preferably at least about 30% or more. Generally, hexasaccharide glycosides I or IV are effective in reducing sensitization when administered at a dosage range of from about 0.5 mg to about 50 mg/kg of body weight, and preferably from about 0.5 mg to about 5 mg/kg of body weight. The specific dose employed is regulated by the sensitization being treated as well as the judgement of the attending clinician depending upon the age and general condition of the patient and the like. "Simultaneous" administration of the compound with the antigen with regard to inhibiting sensitization means that the compound is administered once or continuously throughout a period of time within 3 hours of the administration of an antigen, more preferably the compound is administered within 1 hour of the antigen.

The methods of this invention are generally achieved by use of a pharmaceutical composition suitable for use in the parenteral administration of an effective amount of hexasaccharide glycosides I or IV. These compositions comprise a pharmaceutically inert carrier such as water, buffered saline, etc. and an effective amount of hexasaccharide glycosides I or IV as to provide the above-noted dosage of the oligosaccharide glycoside when administered to a patient. It is contemplated that suitable pharmaceutical compositions can additionally contain optional components such as an adjuvant, a preservative, etc.

It is also contemplated that other suitable pharmaceutical compositions can include oral compositions, transdermal compositions or bandages etc., which are well known in the art.

Hexasaccharide glycosides I and IV containing an analogue of sialic acid are also useful in preparing artificial antigens which can cross-react with antigenic determinants having a similar oligosaccharide structure as in hexasaccharide glycosides I and IV but which contain a naturally occurring sialic acid. Methods for the preparation of artificial antigens and their uses are set forth in U.S. Ser. No. 07/771,007 filed concurrently with this application as attorney docket number 005824-002 and entitled "METHODS FOR THE ENZYMATIC SYNTHESIS OF ALPHA-SIALYLATED OLIGOSACCHARIDE GLYCOSIDES" which application is incorporated herein by reference in its entirety.

The following examples are offered to illustrate the present invention and are not to be construed in any manner as limiting it.

In these examples as well as in the application, all sugars disclosed are in their D form except for fucose which is in its L form.

In these examples, unless otherwise defined below, the abbreviations employed have their generally accepted meaning:

| | |
|---|---|
| CMP-Neu5Ac = | cytidine-5'-monophospho-N-acetylneuraminic acid |
| DTH = | delayed-type hypersensitivity |
| Fuc T = | fucosyl transferase |
| Gal T = | galactosyl transferase |
| GDP-Fuc = | guanosine 5'-diphospho-L-fucose |
| ST = | sialyl transferase |
| U = | Units |
| UDP-Gal = | uridine-5'-diphospho-D-galactose |

AG 1 × 8 (formate form) = ion exchange resin AG 1 × 8 (formate form) available from Bio-Rad Laboratories, Richmond, CA
Dowex 50W × 8 ($H^+$ form) = ion exchange resin Dowex 50W × 8 ($H^+$ form) available from Dow Chemical, Midland, MI
IRC-50 resin ($H^+$ form) = ion exchange resin IRC-50 ($H^+$ form) available from Rohm & Haas, Philadelphia, PA Commercially available components are listed by manufacturer and where appropriate, the order number. Some of the recited manufacturers are as follows:
Iatron = Iatron Laboratories, Tokyo, Japan
Merck = E. Merck AG, Darmstadt, Germany
Millipore = Millipore Corp., Bedford, Mass.
Waters = Waters Associates, Inc., Milford, Mass.

EXAMPLES

The following examples illustrate the preparation of Compounds 5a and 5b which preparation is illustrated in FIG. 1. The synthetic pathway utilized the following general methods:

General Methods: All organic solvents used were re-distilled reagent grade. Pre-coated silica gel plates (60-F254, E. Merck, Darmstadt) were run in 65:35:5, 65:35:8 and/or 60:40:10 mixtures of $CHCl_3$, $CH_3OH$, and 0.2% $CaCl_2$ solution, and detection was by charring after spraying with a 5% solution of sulphuric acid ($H_2SO_4$) in ethanol. Sep-Pak $C_{18}$ cartridges (Waters Associates, Milford, Mass.) were conditioned as indicated by the supplier. Iatrobeads (6RS-8060) were from Iatron Laboratories, Tokyo, Japan and the AG 50W×8 ion exchange resin was purchased from BioRad, Richmond, Calif. CMP-Neu5Ac was purchased from Sigma Chemical Company (St. Louis, Mo.) and GDP-fucose was obtained by chemical synthesis.[59] $\beta$Gal(1–4)$\beta$GlcNAc(1–3)$\beta$Gal-(1–4)$\beta$GlcNAc-OR was obtained by following the procedures of Alais et al[30] with the appropriate substitution of the aglycon. Evaporation of organic solvents was done at 20°–25° C. using a rotory evaporator connected to a water aspirator. $^1$H-n.m.r. spectra have been run on at 300 and 500 MHz using internal acetone ($\delta$=2.225) as reference and samples were freeze dried twice from $D_2O$ and dissolved in 99.99% $D_2O$. The spectra of compounds obtained as 8-methoxycarbonyloctyl glycosides all show a singlet at $\delta$=3.686 ($CO_2CH_3$) and a triplet at $\delta$=2.387 (7.5 Hz, $CH_2CO_2$). The spectra of compounds obtained as the 8-carboxyoctyl glycosides differ from the respective 8-methoxycarbonyloctyl glycosides by the absence of the singlet due to $CO_2CH_3$ and the presence of a triplet at $\delta$=2.314 (t, 7.5 Hz) for $CH_2CO_2H$.

In examples 1 to 6 below, preparative sialylation was conducted as follows:

The rat liver $\beta$Gal(1¾)$\beta$GlcNAc $\alpha$(2–3)sialyl-transferase (EC 2.4.99.5) was purified by affinity chromatography according to the procedure of Mazid, et al.[19] but using a matrix obtained by covalently linking the hapten $\beta$Gal(1–3)$\beta$GlcNAcO$(CH_2)_8CO_2H$[66] activated as in its N-succinimidyl ester to epichlorohydrin activated Sepharose.[67]

The $\beta$Gal(1–4)-$\beta$GlcNAc $\alpha$(2–6)sialyltransferase contained in the flow-through of the above affinity-column, was further chromatographed on CDP-hexanolamine Sepharose as reported.[20]

The enzymatic sialylations were carried out at 37° C. in a plastic tube using a sodium cacodylate buffer (50 mM, pH 6.5) containing Triton CF-54 (0.5%), BSA (1 mg/mL) and calf intestine alkaline phosphatase.[21] The final reaction mixtures were diluted with $H_2O$ and applied onto $C_{18}$ Sep-Pak cartridges as reported.[4] After washing with $H_2O$, the products were eluted with $CH_3OH$ and the solvents evaporated. The residue was dissolved in a 65:35:5 mixture of $CHCl_3$, $CH_3OH$ and $H_2O$ and applied on a small column of Iatrobeads (0.200 to 0.500 g). After washing with the same solvent mixture, the products were eluted with a 65:35:8 and/or 65:40:10 mixtures of the same solvents. The appropriate fractions (t.l.c.) were pooled, the solvents evaporated in vacuo, the residue run through a small column of AG 50W×8 ($Na^+$ form) in $H_2O$ and the products recovered after freeze drying in vacuo. In all cases, the 8-methoxycarbonyloctyl glycosides were separated from the corresponding 8-carboxyoctyl glycosides.

In examples 1 to 6 below, preparative fucosylation was conducted as follows:

The $\beta$GlcNAc $\alpha$(1¾)fucosyltranferase was purified from human milk, as reported.[4] The enzymatic reactions were carried out at 37° C. in a plastic tube using a sodium cacodylate buffer (100 mM, pH 6.5), $MnCl_2$ (10 mM), ATP (1.6 mM), $NaN_3$ (1.6 mM). The reaction products were isolated and purified as indicated above.

Example 1

Preparation of 8-Methoxycarbonyloctyl
(5-Acetamido-3,5-dideoxy-α-D-glycero-D-galacto-2-nonulopyranosylonic
acid)-(2–6)—O—β-D-galactopyranosyl-(1–4)—O—2-acetamido-2-deoxy-glucopyranosyl-(1–3)—O—β-D-galactopyranosyl-(1–4)—O—2-acetamido-2-deoxy-glucopyranoside (2a)

Compound 1a (6.5 mg), CMP-Neu5Ac (17 mg), βGal(1–4)βGlcNAc α(2–6)sialyltransferase (50 mU) and alkaline phosphatase (15 U) were incubated for 48 hours in 2.5 mL of the above buffer. Isolation and purification provided 2a (3.0 mg).

Example 2

Preparation of 8-Methoxycarbonyloctyl
(5-Acetamido-3,5-dideoxy-α-D-glycero-D-galacto-2-nonulopyranosylonic
acid)-(2–6)—O—β-D-galacto-pyranosyl-(1–4)—O—2-acetamido-2-deoxy-glucopyranosyl-(1–3)—O—β-D-galactopyranosyl-(1–4)—O—[α-L-fucopyranosyl-(1–3-)—O—]2-acetamido-2-deoxy-glucopyranoside (3a) and the 8-carboxyoctyl glycoside (3b)

Compound 2a (3.0 mg), GDP-fucose (5 mg), βGlcNAc α(1¾)fucosyltransferase (10 mU) were incubated for 68 hours in the buffer (1.3 mL). Isolation and purification provided 3a (1.2 mg) and 3b (0.5 mg).

Example 3

Preparation of 8-Methoxycarbonyloctyl
β-D-galactopyranosyl-(1–4)—O—2-acetamido-2-deoxy-β-D-glucopyranosyl-(1–3)—O—β-D-galactopyranosyl-(1–4)—O—[α-L-fucopyranosyl-(1–3-)—O—]2-acetamido-2-deoxy-β-D-glucopyranoside (4a) and the 8-carboxyoctyl glycoside (4b)

Compounds 3a and 3b (1.7 mg) were incubated with Clostridium Perfringens neuraminidase immobilized on agarose (Sigma Chemical Company, 1 U) in a buffer of sodium cacodylate (50 mM, pH 5.2, 2 mL) at 37° C. After 24 hours the mixture was diluted with water (10 mL) and filtered through Amicon PM-10 membrane. The flow-through and washings were lyophilized and the residue dissolved in water (3 mL) and applied to two $C_{18}$ cartridge. Each cartridge was washed with water (10 mL) prior to elution with methanol (20 mL). After evaporation of the solvent, the residue was chromatographed on Iatrobeads (210 mg) as indicated above giving (4a, 0.8 mg) and 4b (0.7 mg). 4b was dissolved in dry methanol and treated with diazomethane until t.l.c. indicated the complete conversion into 4a.

Example 4

Preparation of 8-Methoxycarbonyloctyl
(5-Acetamido-3,5-dideoxy-α-D-glycero-D-galacto-2-nonulopyranosylonic
acid)-(2–3)—O—β-D-galactopyranosyl-(1–4)—O—2-acetamido-2-deoxy-β-D-glucopyranosyl-(1–3)—O—β-D-galactopyranosyl-(1–4)—O—[α-L-fucopyranosyl-(1–3)—O—]2-acetamido-2-deoxy-β-D-glucopyranoside (5a) and the 8-carboxyoctyl glycoside (5b)

Compound 4a (1.5 mg), CMP-Neu5Ac (8 mg), βGal(1¾)βGlcNAc α(2–3)sialyltransferase (17 mU), alkaline phosphatase (5 U), were incubated for 40 hours in the sialylation buffer (1.5 mL). Isolation and purification provided 5a (0.7 mg) and 5b (0.55

Example 5

Preparation of 8-Methoxycarbonyloctyl
(5-Acetamido-3,5-dideoxy-α-D-glycero-D-galacto-2-nonulopyranosylonic
acid)-(2–3)—O—β-D-galactopyranosyl-(1–4)—O—2-acetamido-2-deoxy-β-D-glucopyranosyl-(1–3)—O—β-D-galactopyranosyl-(1–4)—O—2-acetamido-2-deoxy-glucopyranoside(6)

Compound 1a (5 mg), CMP-Neu5Ac (15 mg), βGal(1¾)βGlcNAc α(2–3)sialyltransferase (46 mU), and alkaline phosphatase (15 U) were incubated in the sialylation buffer (2,5 mL) for 48 hours. Isolation and purification of the product gave 6a (2.5 mg).

Example 6

Preparation of 8-Methoxycarbonyloctyl
(5-Acetamido-3,5-dideoxy-α-D-glycero-D-galacto-2-nonulopyranosylonic
acid)-(2–3)—O—β-D-galactopyranosyl-(1–4)—O—[α-L-fucopyranosyl-(1–3)—O—]2-acetamido-2-deoxy-glucopyranosyl-(1–3)—O—β-D-galactopyranosyl-(1–4)—O—[α-L-fucopyranosyl-(1–3)—O—]2-acetamido-2-deoxy-glucopyranoside (7a)

Compound 6a (2.5 mg), GDP-fucose (8 mg) and the βGlcNAc α(1→¾)fucosyltransferase (19 mU) were incubated in the enzymatic buffer (2.0 mL) for 48 h. Isolation and purification of the product give 7b (1.7 mg).

$^1$H-NMR data for the compounds prepared in Examples 1 to 6 above are set forth in the following Table I:

TABLE I

| | | $^1$H-n.m.r. Structural Parameters | | | | | | |
|---|---|---|---|---|---|---|---|---|
| Sugar Unit | Hydrogen | 1a | 2a | 3a | 4a | 5a | 6a | 7b |
| βGlcNAc | 1 (d) | 4.516 (8.2) | 4.516 (7.5) | 4.522 (8.0) | 4.525 (7.8) | 4.526 (8.0) | 4.516 (7.5) | 4.527 (7.8) |
| βGal | 1 (d) | 4.457* (7.8) | 4.455* (7.8) | 4.439 (7.8) | 4.436 (7.7) | 4.435 (8.0) | 4.457 (7.7) | 4.434 (7.7) |
| | 4 (d) | 4.157 (3.0) | 4.417 (3.2) | 4.095 (3.0) | 4.098 (3.2) | 4.098 (3.0) | 4.156 (3.2) | 4.092 (3.2) |
| βGlcNAc | 1 (d) | 4.698 (8.2) | 4.728 (7.7) | 4.722 (7.7) | 4.703 (7.7) | 4.692 (8.0) | 4.696 (8.0) | 4.690 (8.3) |
| βGal | 1 (d) | 4.479* (7.8) | 4.462* (7.8) | 4.455 (8.0) | 4.480 (7.7) | 4.457 (7.7) | 4.555 (9.0) | 4.527 (7.8) |
| | 3 (dd) | | | | | 4.114 (3.0, 10.0) | 4.114 (3.0, 9.8) | 4.082 (3.0, 10.0) |
| αFuc | 1 (d) | | | 5.094 (3.7) | 5.096 (3.8) | 5.094 (3.8) | | 5.127, 5.093 (3.8) |
| | 5 (q) | | | 4.814 (6.5) | 4.814 (6.5) | 4.814 (6.5) | | 4.822, 4.818 (6.5) |
| | 6 (d) | | | 1.150 | 1.150 1.152 | 1.150 | | 1.170, 1.144 |
| αNeu5Ac(2-3) | $3_{ax}$ (dd) | | | | | 2.756 (4.5, | 2.758 (4.5, | 2.762 (4.5, 12.7) |

TABLE I-continued

$^1$H-n.m.r. Structural Parameters

| Sugar Unit | Hydrogen | 1a | 2a | 3a | 4a | 5a | 6a | 7b |
|---|---|---|---|---|---|---|---|---|
|  | $3_{eq}$ (t) |  |  |  |  | 13.0) | 12.5) | 1.792 (12.0) |
|  |  |  |  |  |  | 1.796 (12.0) | 1.796 (12.2) |  |
| αNeu5Ac(2-6) | $3_{ax}$ (dd) |  | 2.670 (4.5, 12.5) | 2.666 (4.5, 12.5) |  |  |  |  |
|  | $3_{eq}$ (t) |  | 1.720 (12.0) | 1.718 (12.0) |  |  |  |  |
| NAc | (s) | 2.028 | 2.027 (two) | 2.021, 2.026 | 2.027 | 2.024 | 2.030 | 2.012, 2.018 |
|  |  | 2.033 | 2.055 | 2.043 | 2.032 | (three) | (three) | 2.028 |
| $CH_2CO_3$ | (t) | 2.388 (7.5) | 2.387 (7.5) | 2.387 (7.5) | 2.386 (7.5) | 2.386 (7.5) | 2.387 (7.5) | 2.314 (7.5) |
| $CO_2R$ |  | $CH_3$ | $CH_3$ | $CH_3$ | $CH_3$ | $CH_3$ | $CH_3$ | H |
|  |  | 3.685 | 3.686 | 3.686 | 3.688 | 3.686 | 3.684 |  |

*interchangeable

KINETIC DATA

Experiments were conducted to determine the relative rates of transfer of fucosylation onto the 3-hydroxy of the GlcNAc in disaccharide glycosides βGal(-1-4)βGlcNAc-OR having different substituents at the 6-position of the galactose. Fucosyltransferase assays were conducted with α(1¾)fucosyltransferase in a manner similar to that described in the art[4] and gave the following results:

| Substituent at the 6-position of galactose | R | Relative Rate of Transfer |
|---|---|---|
| —OH | —$(CH_2)_8CO_2CH_3$ | 100 |
| H | —$(CH_2)_2O(CH_2)_2CO_2CH_3$ | 9 |

The remaining low relative rate of transfer obtained on the 6'-deoxy derivative may be due to a small amount of βGal α(1-2)fucosyltransferase which was present in the preparation of the α(1¾)fucosyltransferase.

The above results indicate that the presence of a hydroxyl group at the 6-position of galactose is necessary for efficient fucosylation of 3-hydroxy of the GlcNAc in disaccharide glycosides βGal(1-4)βGlcNAc-OR using α(1¾)fucosyltransferase.

The following Examples 7 to 8 illustrate alternative methods for preparing for compounds of Formula I.

In these examples, during the chemical synthesis, unless otherwise specially indicated, the work up generally included extraction with dichloromethane followed by the normal sequential washings of the organic phase with water, a dilute solution of sodium carbonate and water. The organic solvent were then dried over magnesium sulfate, the solid filtered and the solvent evaporated in vacuo as indicated.

Evaporation of organic solvents was done at 20°–25° C. using a rotory evaporator connected to a water aspirator. $^1$H-n.m.r. spectra were run at 300 MHz using internal acetone (δ=2.225) as reference and samples were freeze dried twice from D$_2$O and dissolved in 99.99% D$_2$O. The spectra of compounds obtained as 8-methoxycarbonyloctyl all show a singlet at δ=3.686 (CO$_2$CH$_3$) and a triplet at δ=2.387 (7.5 Hz, CH$_2$CO$_2$). The spectra of compounds obtained as the 8-carboxyoctyl glycosides differ from the respective 8-methoxycarbonyloctyl glycosides by the absence of the singlet due to CO$_2$CH$_3$ and the presence of a triplet at δ=2.314 (t, 7.5 Hz) for CH$_2$CO$_2$H.

Preparative Enzymatic Sialylation

The rat liver βGal(1¾)βGlcNAc α(2-3)sialyltransferase (EC 2.4.99.5) was purified by affinity chromatography according to the procedure of Mazid, et al.[19] but using a matrix obtained by covalently linking the hapten βGal(1-3)βGlcNAcO(CH$_2$)αCO$_2$H[66] activated as in its N-succinimidyl ester to epichlorohydrin activated Sepharose.[67] The enzymatic sialylations were carried out at 37° C. in a plastic tube using a sodium cacodylate buffer (50 mM, pH 6.5) containing Triton CF-54 (0.5%), BSA (1 mg/mL) and calf intestine alkaline phosphatase.[69] The final reaction mixtures were diluted with H$_2$O and applied onto C$_{18}$ Sep-Pak cartridges as reported.[4] After washing with H$_2$O, the products were eluted with CH$_3$OH and the solvents evaporated. The residue was dissolved in a 65:35:5 mixture of CHCl$_3$, CH$_3$OH and H$_2$O and applied on a small column of Iatrobeads (0.200 to 0.500 g). After washing with the same solvent mixture, the products were eluted with a 65:35:8 and/or 65:40:10 mixtures of the same solvents. The appropriate fractions (t.l.c.) were pooled, the solvents evaporated in vacuo, the residue run through a small column of AG 50W×8 (Na$^+$form) in H$_2$O and the products recovered after freeze drying in vacuo. In all cases, the 8-methoxycarbonyloctyl glycosides were separated from the corresponding 8-carboxyoctyl glycosides.

Preparative Enzymatic Fucosylation

Enzymatic Conditions

The βGlcNAc α(1¾)fucosyltransferase (EC 2.4.1.65) was purified from human milk, as reported.[4] The enzymatic reactions were carried out at 37° C. in a plastic tube using a sodium cacodylate buffer (100 mM, pH 6.5), MnCl$_2$ (10 mM), ATP (1.6 mM), NaN$_3$ (1.6 mM). The reaction products were isolated and purified as indicated above.

Synthesis of GDP-Fucose

A. Preparation of Bis(tetra-n-butylammonium) hydrogen phosphate

Tetra-n-butylammonium hydroxide (40% aq. w/w, about 150 g) was added dropwise to a solution of phosphoric acid (85% aq, w/w, 18 g, 0.155 mmol) in water (150 mL) until the pH reached 7. Water was then evaporated in vacuo to give a syrup which was co-evaporated with dry acetonitrile (2×400 mL) followed by dry toluene (2×400 mL). The resulting white solid (75 g) was dried in vacuo and stored over phosphorus pentoxide under vacuum until used.

B. Preparation of β-L-Fucopyranosyl-1-Phosphate

A solution of bis(tetra-n-butylammonium) hydrogen phosphate (58 g, 127.8 mmol) in dry acetonitrile (300 mL) was stirred at room temperature under nitrogen in the presence of molecular sieves (4Å, 20 g) for about one hour. A solution of tri-O-acetyl fucosyl-1-bromide (freshly prepared from 31 g, 93 mmol of L-fucose tetraacetate in the manner of Nunez et al.[72]) in dry toluene (100 mL) was added dropwise in about 0.5 hour to the above solution, cooled at 0° C. After one more hour at 0° C., the mixture was brought to room temperature and stirred for 3 hour. Tlc (1:1 toluene:ethyl acetate) indicated a main spot on the base line and several faster moving smaller spots.

The mixture was filtered over a pad of Celite (which was further washed with acetonitrile) and the solvents evaporated in vacuo to give a red syrup. This material was dissolved in water (400 mL) and extracted with ethyl acetate (250 mL, twice). The aqueous layer was then evaporated in vacuo leaving a yellowish syrup to which a solution of ammonium hydroxide (25% aq., 200 mL) was added. The mixture was stirred at room temperature for 3 hours after which tlc (65:35:8 chloroform:methanol:water) indicated a baseline spot. The solvent was evaporated in vacuo to give a yellowish syrup which was diluted with water (400 mL). The pH of this solution was checked and brought to 7, if necessary, by addition of a small amount of hydrochloric acid. The solution was slowly absorbed onto a column of ion exchange resin Dowex 2×8 [200–400 mesh, 5×45 cm, bicarbonate form which had been prepared by sequential washing of the resin with methanol (800 mL), water (1200 mL), ammonium bicarbonate (1 M, 1600 mL) and water (1200 mL)]. Water (1000 mL) was then run through the column followed by a solution of ammonium bicarbonate (0.5 M, 2.3 mL/minute, overnight). The eluate was collected in fractions (15 mL) and the product detected by charting after spotting on a tlc plate. Fractions 20 to 57 were pooled and evaporated in vacuo leaving a white solid which was further co-evaporated with water (3×300 mL) and freeze drying of the last 50 mL and then drying of the residue with a vacuum pump to give $\beta$-L-fucopyransyl-1-phosphate (9.5 g, 40%) as a 12:1 mixture of $\beta$ and $\alpha$ anomers containing some ammonium acetate identified by a singlet at $\delta = 1.940$ in the $^1$H-n.m.r. spectrum. This product was slowly run through a column of Dowex 5×8 resin (100–200 mesh, triethylammonium form) and eluted with water to provide the bis triethylammonium salt of $\beta$-L-fucopyransyl-1-phosphate as a sticky gum after freeze drying of the eluate. $^1$H-n.m.r. $\delta$:4.840 (dd, $J_{1,2}=J_{1,p}=7.5$ Hz, H-1), 3.82 (q, 1H, $J_{5,6}$ 6.5 Hz, H-5), 3.750 (dd, 1H, $J_{3,4}$ 3.5, $J_{4,5}$ 1.0 Hz, H-4), 3.679 (dd, 1H, $J_{2,3}$ 10.0 Hz, H-3), 3.520 (dd, 1H, H-2), 1.940 (s, acetate), 1.26 (d, H-6). Integral of the signals at 3.20 (q, J 7.4 Hz, NCH$_2$) and 1.280 and 1.260 (NCH$_2$CH$_3$ and H-6) indicates that the product is the bis-triethylammonium salt which may loose some triethylamine upon extensive drying. $^{13}$C-n.m.r. $\delta$:98.3 (d, $J_{C,1P}$ 3.4 Hz, C-1), 72.8 (d, $J_{C,2P}$ 7.5 Hz, C-2), 16.4 (C-6); $^{31}$P-nmr $\delta$: +2.6(s).

$\beta$-L-fucopyransyl-1-phosphate appears to slowly degrade upon prolonged storage (1 + days) in water at 22° C. and, accordingly, the material should not be left, handled or stored as an aqueous solution at 22° C. or higher temperatures. In the present case, this material was kept at −18° C. and dried in vacuo over phosphorus pentoxide prior to being used in the next step.

C. Preparation of Guanosine 5'-($\beta$-1-Fucopyranosyl)-Diphosphate

Guanosine 5'-($\beta$-1-fucopyranosyl)-diphosphate was prepared from $\beta$-L-fucopyranosyl-1-phosphate using two different art recognized procedures as set forth below:

PROCEDURE #1

$\beta$-L-fucopyranosyl-1-phosphate and guanosine 5'-mono-phosphomorpholidate (4-morpholine-N,N'-dicyclohexyl-carboxamidine salt, available from Sigma, St. Louis, Mo., "GMP-morpholidate") were reacted as described in a recent modification[74,75] of Nunez's original procedure[72]. Accordingly, tri-n-octylamine (0.800 g, available from Aldrich Chemical Company, Milwaukee, Wis.) was added to a mixture of $\beta$-L-fucopyranosyl-1-phosphate (triethylammonium salt, 1.00 g, about 2.20 mmol) in dry pyridine (10 mL) under nitrogen the solvent removed in vacuo. The process was repeated three times with care to allow only dry air to enter the flask. GMP morpholidate (2.4 g, about 3.30 mmol) was dissolved in a 1:1 mixture of dry dimethylformamide and pyridine (10 mL). The solvents were evaporated in vacuo and the procedure repeated three times as above. The residue was dissolved in the same mixture of solvents (20 mL) and the solution added to the reaction flask accompanied by crushed molecular sieves (2 g, 4Å). The mixture was stirred at room temperature under nitrogen. Tlc (3:5:2 25% aq. ammonium hydroxide, isopropanol and water) showed spots corresponding to the starting GMP-morpholidate (Rf~0.8, U.V.), guanosine 5'-($\beta$-1-fucopyranosyl)-diphosphate (Rf~0.5, U.V. and charring), followed by the tailing spot of the starting fucose-1-phosphate (Rf~0.44, charring). Additional U.V. active minor spots were also present. After stirring for 4 days at room temperature, the yellowish mixture was co-evaporated in vacuo with toluene and the yellowish residue further dried overnight at the vacuum pump leaving a thick residue (2.43 g). Water (10 mL) was then added into the flask to give a yellow cloudy solution which was added on top of a column of AG 50W-X12 (from Biorad) resin (100–200 mesh, 25×1.5 cm, Na+form). The product eluted with water after the void volume. The fractions which were active, both by U.V. and charring after spotting on a tlc plate, were recovered and the solution freeze-dried overnight in vacuo providing a crude material (1.96 g).

This residue was dissolved in water (10 mL overall) and slowly absorbed onto a column of hydrophobic C$_{18}$ silica gel (Waters, 2.5×30 cm) which had been conditioned by washing with water, methanol and water (250 mL each). Water was then run through the column (0.4 mL/min) and the eluate collected in fractions (0.8 mL) which were checked by tlc (3:5:2 25% aq. ammonium hydroxide, isopropanol and water). $\beta$-L-fucopyranosyl-1-phosphate, (Rf~0.54, charting) was eluted in fractions 29 to 45. A product showing a strongly U.V. active spot (Rf~0.51) eluted mainly in fractions 46 to 65. Other minor U.V. active spots of higher or lower Rf were observed. Fractions 59 to 86, which contained guanosine 5'-($\beta$-1-fucopyranosyl)-diphosphate (Rf~0.62), also showed a narrow U.V. active spot (Rf~0.57). Fractions 59 to 86 were pooled and freeze-dried overnight providing 0.353 g of material enriched in guanosine 5'-($\beta$-1-fucopyranosyl)-diphosphate. $^1$H-n.m.r. indicated that this material was contaminated by a small amount of impurities giving signals at δ=4.12 and δ=5.05.

Fractions 29 to 45 and 47 to 57 were separately pooled and freeze-dried providing recovered β-L-fucopyranosyl-1-phosphate (0.264 g and 0.223 g, respectively, in which the second fraction contains some impurities). Occasionally, pooling of appropriate fractions provided some amount of guanosine 5'-(β-1-fucopyranosyl)-diphosphate in good purity ($^1$H-n.m.r.). Generally, all the material enriched in guanosine 5'-(β-1-fuco-pyranosyl)diphosphate was dissolved in a minimum amount of water and run on the same column which had been regenerated by washing with large amounts of methanol followed by water. The fractions containing the purified guanosine 5'-(β-1-fucopyranosyl)-diphosphate (tlc) were pooled and freezed dried in vacuo leaving a white fluffy material (187 mg, 16%). $^1$H-n.m.r. was identical to the previously reported data[73].

PROCEDURE #2

β-L-fucopyranosyl-1-phosphate and guanosine 5'-monophosphomorpholidate (4-morpholine-N,N'-dicyclohexyl-carboxamidine salt —"GMP-morpholidate") were reacted in dry pyridine as indicated in the original procedure[22]. Accordingly, the β-L-fucopyranosyl-1-phosphate (triethylammonium salt, 0.528 g, about 1.18 mmol) was dissolved in dry pyridine (20 mL) and the solvent removed in vacuo. The process was repeated three times with care to allow only dry air to enter the flask. GMP-morpholidate (1.2 g, 1.65 mmol) and pyridine (20 mL) were added into the reaction flask, the solvent evaporated in vacuo and the process repeated three times as above. Pyridine (20 mL) was added to the final residue and the heterogeneous mixture was stirred for 3 to 4 days at room temperature under nitrogen. An insoluble mass was formed which had to be occasionally broken down by sonication.

The reaction was followed by tlc and worked up as indicated in the first procedure to provide the GDP-fucose (120 mg, 16%).

Preparative Enzymatic Galactosylation

The bovine milk βGlcNAc 5(1-4) galactosyltransferase (EC 2.4.1.22, specific activity 6.5 units/mg of protein) and UDP-Gal were obtained from Sigma. The enzymatic reactions were carried out at 37° C. in a plastic tube using a sodium cacodylate buffer (100 mM, pH 7.5) containing 20 mM manganese dichloride. The reaction products were purified as indicated above in the case of the preparative sialylation.

In some cases, depending upon the enzymatic preparation, it may happen that the terminal methyl ester of the aglycone is hydrolyzed. As a result, the final products may possibly be isolated as saccharides possessing the aglycone terminated by a methyl ester or a free acid group. These two saccharides are separated during the step of the chromatography on Iatrobeads as indicated above. The two forms of the aglycone of the saccharide are identified by $^1$H-n.m.r.

Example 7

Synthesis of 8-Methoxycarbonyloctyl (2,3,4,6-tetra—O—acetyl-β-D-galactopyranosyl)-(1–4)—O—3,6-di—O—acetyl-2-deoxy-2-phthalimido-β-D-glucopyranoside (Compound 19)

A. Synthesis of Compound 12

A solution of trimethylsilyltrifluoromethanesulfonate (0.504 mL, 2.6 mmol) in dichloromethane (4 mL) was added to the mixture of the disaccharide donor 11[30] (2.0 g, 2.6 mmol), drierite (4.0 g, crushed) and 8-methoxycarbonyl-octanol (1.9 g, 10.0 mmol) in dichloromethane (30 mL) at 4° C. After stirring for 0.5 h at 4° C., the mixture was slowly warmed up to room temperature for 1 h. After cooling to 4° C., a second portion of the catalyst (0.250 mL, 1.3 mmol) in dichloromethane (2 mL) was added. After slowly warming up and stirring at room temperature for 1 h, the reaction was stopped by addition of triethylamine. After filtration, the crude product recovered after the usual work up was dried in vacuo, and acetylated in a 2:1 mixture of pyridine and acetic anhydride. After addition of methanol, the mixture was worked up as usual, and the solvents co-evaporated with an excess of toluene. The residue was chromatographed on silica gel using a 2:1 mixture of toluene and ethyl acetate providing compound 12 (1.40 g, 60%). $^1$H-n.m.r. (CDCl$_3$): δ7.90–7.70 (m, 4H, aromatics), 5.75 (dd, 1H, J$_{2,3}$ 10.5 J$_{3,4}$ 9.5Hz, H-3), 5.34(m, 2H, incl. H-1 and H-4'), 5.15(dd, 1H, J$_{1',2'}$8.0, J$_{2',3'}$10.5 Hz, H-2'), 4.97(dd, 1H, H-3'), 3.67(s, 3H, CO$_2$CH$_3$), 2.25(t, 2H, J 7.5 Hz, CH$_2$CO$_2$), 2.19–1.94(6s, 18H, 6OAc), 1.45 (m, 4H) and 1.08 (m, 8H): methylenes.

Synthesis of Compound 5—8-Methoxycarbonyloctyl (2,6-di—O—acetyl-3,4—O—isopropylidene-β-D-galactopyranosyl)-(1–4)—O—(3,6-di—O—acetyl-2-deoxy-2-phthalimido-β-D-glucopyranoside (15)

A 1M solution of sodium methoxide in methanol (0.200 mL) was added to a solution of compound 12 (1.40 g, 1.65 mmol) in methanol (40 mL) cooled at 4° C. After 1.5 h at 4° C., the solution was deionized using IRC-50 resin (H$^+$ form). The resin was filtered, the solvent evaporated and the product dried in vacuo (1.0 g, 94%).

A solution of the above material (0.776 g, 1.2 mmol) and paratoluene sulfonic acid monohydrate (60 mg) in dry acetone (60 mL) was refluxed for 3 h. After neutralization with triethylamine, the solvent was evaporated and the residue chromatographed on silica gel using a 100:1 mixture of ethyl acetate and methanol providing compound 14 (0.575 g, 70%); $^1$H-n.m.r. (CD$_3$OD, DOH at 4.80): 7.80–7.60 (m, 4H, aromatics), 5.10 (d, 1H, J$_{1,2}$8.0 Hz, H-1), 4.38 (m, 2H, H-1 and H-3), 3.70(s, 3H, CO$_2$CH$_3$), 2.31(t, J 7.5 Hz, CH$_2$CO$_2$), 1.65–1.00[m, incl. 1.57 and 1.45 (2s, C(CH$_3$)$_2$]. Further elution provided the 4,6-isopropylidene derivative (0.200 g, 24%).

Compound 14 (0.515 g, 0.84 mmol) was acetylated in a 2:1 mixture of pyridine and acetic anhydride for 24 h at 22°. After addition of methanol and the usual work up, the solvents were co-evaporated with an excess of toluene and the residue chromatographed on silica gel using a 100:3 mixture of chloroform and methanol providing compound 15 (0.646 g, 90%); [α]$_D$+13.8° (c, 1 chloroform); $^1$H-n.m.r. (CDCl$_3$); δ7.90–7.70 (m, 4H, aromatics), 5.74 (J$_{1,2}$8.5,, J$_{2,3}$ 10.5 Hz, H-3), 5.34 (d, 1H J$_{1,2}$ 8.5 Hz, H-1), 4.88 (dd, 1H, J$_{1',2'}$~J$_{2',3'}$ 6.5 Hz, H-2'), 3.67(s, 3H, CO$_2$CH$_3$), 2.23(t, J 7.5 Hz, CH$_2$CO$_2$), 2.14, 2.13, 2.10, 1.91(4s, 12H, 4 OAc), 1.30–1.54 [m, incl. 1.53 and 1.32 (2s, C(CH$_3$)$_2$].

C. Synthesis of Compound 16—8-Methoxycarbonyloctyl (2,6-di-O-acetyl-β-D-galactopyranosyl)-(1–4)—O—3,6-di-O-acetyl-2-deoxy-2-phthalimido-β-D-glucopyranoside Compound 15 (0.575 g, 0.68 mmol) in 90% acetic acid (12 mL) was heated at 80° for 2 h. After dilution with dichloromethane, the solvent was washed with water, a solution of sodium bicarbonate and water. After drying over magnesium sulfate, the solvents were evaporated in vacuo, and the residue chromatographed on silica gel providing compound 16 (0.452 g, 82%); [α]$_D$ +12.1 (c, 1.03 chloroform).

D. Synthesis of Compound 8—8-Methoxycarbonyloctyl (3,4,6-tri-O-acetyl-2-deoxy-2-phthalimido-β-D-glucopyranosyl)-(1–3)—O—(2,6-di—O—acetyl-β-D-galactopyranosyl)-(1–4)—O—3,6-di—O—acetyl-2-deoxy-2-phthlamido-β-D-glucopyranoside (18)

Trimethylsilyltrifluoromethanesulfonate (0.036 mL, 0.060 mmol) in methylene chloride (0.5 mL) was added to a solution of compound 16 (0.100 g, 0.123 mmol) in methylene chloride (5 mL). A solution of the imidate 17 (0.102 g, 0.185 mmol) in methylene chloride (4 mL) was slowly added to the above solution cooled at −70°. The mixture was further stirred at that temperature for 0.5 h. An additional portion of the catalyst (0.018 mL, 0.030 mmol) in methylene chloride (0.5 mL) was further added. After 0.5 h at −70°, the reaction was stopped by addition of triethylamine, and the mixture worked up as usual. The recovered residue was chromatographed on silica gel using a 100:2 mixture of chloroform and methanol providing compound 18 (0.120 g, 80%); $^1$H-n.m.r. (CDCl$_3$): δ7.95–7.60 (m, 8H, aromatics), 5.74 (dd, 1H, J$_{2'',3''}$10.5 J$_{3'',4''}$ 9.0 Hz, H-3''), 5.61(dd, 1H, J$_{2,3}$ 10.5, J$_{3,4}$ 8.5 Hz, H-3), 5.48(d, 1H, J$_{1'',2''}$ 8.5 Hz, H-1''), 5.27 (d, 1H, J$_{1,2}$ 8.5 HZ, H-1), 5.14 (dd, 1H, J$_{4'',5''}$ 10.0 Hz, H-4''), 4.90(dd, 1H, J$_{1',2'}$ 8.0 J$_{3',4'}$ 10.0 Hz, H-2'), 3.68(s, CO$_2$CH$_3$), 0.22(t, J 7.5 Hz, CH$_2$CO$_2$), 2.12(two), 2.10, 2.04, 1.86, 1.85, 1,56(6s, 21H, 7 OAc), 1.40 (m, 4H), and 1.20 (m, 8H): methylenes.

E. Synthesis of Compound 19—8-Methoxycarbonyloctyl (2-acetamido-2-deoxy-β-D-glucopyranosyl)-(1–3-)—O—(β-D-galactopyranosyl)-(1–4)—O—2-acetamido-2-deoxy-β-D-glucopyranoside Hydrazine acetate (1.27 g, 13.8 mmol) was added to compound 18 (0.120 g, 0.098 mmol) in anhydrous ethanol (15 mL). The mixture was refluxed for 18 h. The solvents were then co-evaporated with an excess of toluene. After drying in vacuo, the residue was acetylated in a 2:1 mixture of pyridine and acetic anhydride for 48 h. After quenching the excess of acetic anhydride with some methanol, the reaction mixture was worked up as usual. The recovered solvents were evaporated in vacuo and the residue co-evaporated with an excess of toluene. The residue was chromatographed on silica gel using a 100:9 mixture of chloroform and methanol as eluant provided the peracetylated trisaccharide intermediate. This material was de—O—acetylated in anhydrous methanol (5 mL) in the presence of 0.2 M sodium methoxide in methanol (0.200 mL). After overnight at 22° C., de-ionization with Dowex 50×8 and filtration, the solvent was evaporated in vacuo. The recovered product was chromatographed on BioGel P-2 and eluted with a 1:1 mixture of water and ethanol which provided the pure trisaccharide 19 (0.044 g, 60%); [α]$_D$ −4.8° (c, 0.48, water); $^1$H-n.m.r. (D$_2$O): data provided in Table II.

Example 8

Synthesis of 8-Methoxycarbonyloctyl (5-acetamido-3,5-dideoxy-β-D-glycero-D-galacto-2-nonulopyranosylonic acid)-(2–3)—O—(β-D-galactopyranosyl)-(1–4)—O—(2-acetamido-2-deoxy-β-D-glucopyranosyl)-(1–3)—O—(β-D-galactopyranosyl)-(1–4)—O—[β-L-fucopyranosyl-(1–3)—O]-2-acetamido-2-deoxy-β-D-glucopyranoside (22) (Compound) 22—the CD-65/VIM-2 Saccharide)

A. Synthesis of Compound 20—8-Methoxycarbonyloctyl (2-acetamido-2-deoxy-β-D-glucopyranosyl)-(1–3-)—O—(β-D-galactopyranosyl)-(1–4)—O—[α-L-fucopyranosyl-(1–3)—O]-2-acetamido-2-deoxy-β-D-glucopyranoside Compound 19 (15 mg), GDP-fucose (33 mg) and the βGlcNAc α(1¾)fucosyltransferase (56 mU) were incubated for 72 hours in the buffer (4 mL) as indicated above. Isolation and purification provided the compound 20 (14.0 mg). $^1$H-n.m.r. data is included in Table II.

B. Synthesis of Compound 21—8-Methoxycarbonyloctyl (β-D-galactopyranosyl)-(1–4)—O—(2-acetamido-2-deoxy-β-D-glucopyranosyl)-(1–3)—O—(β-D-galactopyranosyl)-(1–4)—O—[β-L-fucopyranosyl-(1–3-)—0]-2-acetamido-2-deoxy-β-D-glucopyranoside Compound 20 (14.0 mg), UDP-Gal (25 mg), βGlcNAc (1–4) galactosyltransferase (14.5 U, Sigma) were incubated for 48 hours in the buffer described above (3.2 mL). Isolation and purification provided compound 21 (13.2 mg). $^1$H-n.m.r. data is included in Table II.

C. Synthesis of Compound 22—8-Methoxycarbonyloctyl (5-acetamido-3,5-dideoxy-α-D-glycero-D-galacto-2-nonulopyranosylonic acid)-(2–3)—O—(β-D-galactopyranosyl)-( 1–4)—O—(2-acetamido-2-deoxy-β-D-glucopyranosyl)-(1–3)—O—(β-D-galacto-pyranosyl)-(1–4)—O—[α-L-fucopyranosyl-(1–3)—O]-2-acetamido-2-deoxy-β-D-glucopyranoside Compound 22 was synthesized from compound 21 as indicated above[65].

TABLE II

| | $^1$H-n.m.r. Structural Parameters | | | |
|---|---|---|---|---|
| Sugar Unit | Hydrogen | 19$^{a,b}$ | 20$^{a,b}$ | 21$^{a,b}$ | 22$^{a,b}$ |
| βGlcNAc (A) | 1 (d) | 4.50$^c$ (7.5) | 4.52 (7.5) | 4.52 (8.0) | 4.53 (8.0) |
| βGal (B) | 1 (d) | 4.45$^c$ (8.0) | 4.43 (7.0) | 4.43 (7.5) | 4.43 (8.0) |
| | 4 (d) | 4.15 (3.0) | 4.09 (3.5) | 4.10 (3.2) | 4.10 (3.0) |
| βGlcNAc (C) | 1 (d) | 4.66 (8.5) | 4.67 (8.5) | 4.70 (7.8) | 4.69 (8.0) |
| βGal (D) | 1 (d) | | | 4.48 (7.8) | 4.46 (7.7) |
| | 3 (d) | | | | |
| αFuc | 1 (d) | | 5.09 (4.0) | 5.10 (3.8) | 5.09 (3.8) |

TABLE II-continued

| Sugar Unit | Hydrogen | $19^{a,b}$ | $20^{a,b}$ | $21^{a,b}$ | $22^{a,b}$ |
|---|---|---|---|---|---|
| | 5 (q) | | 4.81 (6.5) | 4.81 (6.5) | 4.81 (6.5) |
| | 6 (d) | | 1.14 | 1.15 | 1.15 |
| αNeu5Ac | $3_{ax}$ (dd) | | | | 2.76 (4.5, 13.0) 1.79 |
| | $3_{eq}$ (t) | | | | (12.0) |
| NHAc | s | 2.02, 2.01 | 2.02, 2.01 | 2.03, 2.02 | 2.02 (three) |
| $CH_2CO_2$ | t | 2.38 (7.5) | 2.38 (7.5) | 2.38 (7.5) | 2.38 (7.5) |
| $CO_2CH_3$ | s | 3.68 | 3.69 | 3.69 | 3.69 |

[a]9, 10, 11 and 12 show multiplets around 1.49–1.63 (4H) and 1.30 (8H): methylenes
[b]J in Hz
[c]interchangeable

C. IMMUNOSUPPRESSIVE PROPERTIES

Examples 9 and 10 illustrate the immunosuppressive properties of hexasaccharide glycoside 5a.

Example 9

Inhibition of DTH Inflammatory Response

DTH inflammatory responses were measured using the mouse footpad swelling assay as described by Smith and Ziola[31]. Briefly, groups of Balb/c mice were immunized with 10 μg of the L111 S-Layer protein, a bacterial surface protein[32] from *Clostridium thermohydrosulfurum* L111-69 which has been shown to induce a strong inflammatory DTH response. Seven days later, each group of mice was footpad-challenged with 10 μg of L-111 S-Layer protein. The resulting inflammatory footpad swelling was measured with a Mitutoyo Engineering micrometer 24 hours after challenge.

To assess the effect of hexasaccharide glycoside 5a on the inflammatory DTH response, groups of mice received 100 μg of this compound, injected into the tail vein, 5 hours after challenge. Control groups received 100 μL of phosphate-buffered saline (PBS). The results of this experiment are shown in Table III below. In this table, smaller increases in footpad swelling, as compared to control, evidence the fact that the tested compound possesses immunosuppressive properties in that it reduces the degree of footpad swelling in response to an antigen.

TABLE III

| COMPOUND TESTED | INCREASE IN FOOTPAD SWELLING (mm−1) |
|---|---|
| Control | 3.3 |
| Hexasaccharide Glycoside 5a | 1.5 |

The above results indicate that mice injected with hexasaccharide glycoside 5a had less than 50% of the footpad swelling as compared to the control mice.

Example 10

Persistence of Suppression of the DTH Inflammatory Response at 11 Weeks After Challenge i. The identical groups of mice treated with hexasaccharide glycoside 5a in Example 7 were rechallenged with L111 S-Layer protein 11 weeks after primary immunization. Mice treated with the PBS control responded with the usual degree of footpad swelling whereas mice treated with hexasaccharide glycoside 5a showed a reduction in footpad swelling of about 40%, i.e., the mice treated with hexasaccharide glycoside 5a exhibited only about 60% of the footpad swelling exhibited in mice treated with PBS.

This anti-inflammatory effect of hexasaccharide glycosides 5a, given 5 hours after the first challenge (one week after primary immunization), had somewhat weakened eleven weeks after primary immunization but nevertheless provided for a significant reduction in inflammation as compared to PBS treated controls.

In addition to providing suppression of cell-mediated immune responses, the above data demonstrate that treatment with a hexasaccharide glycoside as per this invention also imparts tolerance to additional challenges from the same antigen.

Example 11

Effect Hexasaccharide Glycoside 5a has on ELAM-1 Dependent Cell Adhesion to Activated Vascular Endothelium This example examines whether hexasaccharide 5a could inhibit ELAM-1 dependent cell adhesion to activated vascular endothelium. Specifically, an vitro cell binding assay was preformed as described by Lowe et al[33]. Briefly, human umbilical vein endothelial cells (HUVECs purchased from Cell Systems, Seattle, Wash., USA) were stimulated with TNFα (10 ng/ml) to express ELAM-1. Human tumor cell lines, U937 or HL60, which have been shown to bind to HUVECs, in an ELAM-1 dependent manner were used to measure the effect that hexasaccharide glycoside 5a has on the ELAM-1 dependent binding to the HUVEC. The results of this example demonstrate that hexasaccharide glycoside 5a inhibits ELAM-1 dependent binding to the HUVECs.

The data in Examples 9 and 10 above establish the effectiveness of the hexasaccharide glycosides described herein in treating immune responses to an antigen and in inducing tolerance to the antigen in a mammal (mice). In view of the fact that the immune system of mice is a good model for the human immune system, such hexasaccharide glycosides will also be effective in treating human immune responses. This is borne out by the fact that Example 11 establishes that hexasaccharide glycoside 5a inhibits ELAM-1 dependent binding to the HUVEC.

By following the procedures set forth in the above examples, hexasaccharide glycosides of formula I and IV above could be used to suppress a cell-mediated immune response to an antigen by mere substitution for hexasaccharide glycoside 5a described in these examples.

The compounds defined by formula II, III, V and VI are useful at least as intermediates in the preparation of compounds I and IV. Similarly, the transfer of L-fucose via a (1-3)fucosyltransferase can employ a compatible analog of L-fucose which is recognized by the transferase and provides for products wherein Y and Y' are compatible analogs of L-fucose.

What is claim is:

1. A method for preparation of a compound of the formula I:

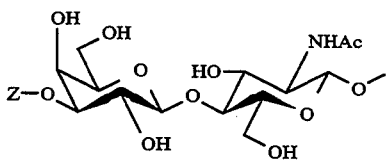

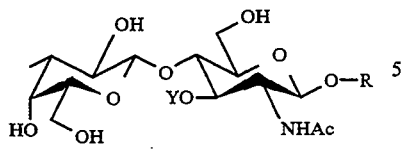

wherein R is hydrogen, a saccharide, an oligosaccharide or an aglycon group having at least one carbon atom, Y is L-fucose or a compatible analogue of L-fucose, and Z is sialic acid or a compatible analogue of sialic acid, which method comprises (a) fucosylating a compound of the formula II

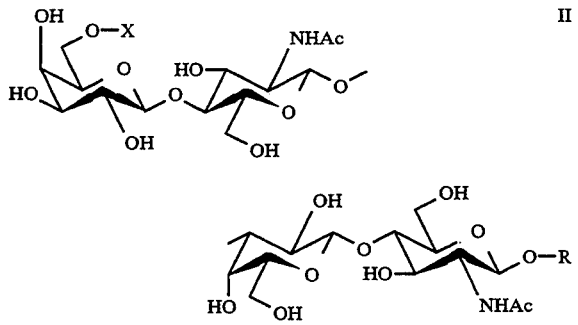

wherein R is as defined above and X is a removable blocking group with an α(1-3)fucosyltransferase in the presence of a compatible GDP derivative of L-fucose or an analogue thereof under conditions wherein the L-fucose is transferred to the 3-position of the N-acetylglucosamine unit at the reducing sugar terminus so as to form a monofucosylated derivative of the formula III:

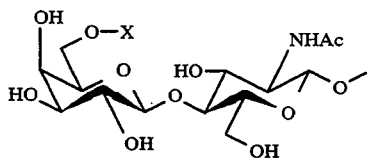

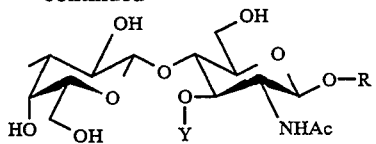

wherein X, Y and R are as defined above;

(b) removing the removable blocking group from the compound formed in (a) above; and (c) sialylating the compound formed in (b) above with sialic acid or a compatible analogue of sialic acid in the presence of a compatible CMP-derivative of sialic acid or an analogue thereof using an α(2-3)-sialyltransferase under conditions wherein the sialic acid or analogue thereof is transferred to the 3 position of the theretofore terminal galactose unit so as to form the compound of formula I.

2. A method according to claim 1 wherein R is selected from the group consisting of —(A)—Z' wherein A represents a bond, an alkylene group of from 2 to 10 carbon atoms, and a moiety of the form —(CH$_2$-CR$_2$G)$_n$— wherein n is an integer equal to 1 to 5; R$_2$ is selected from the group consisting of hydrogen, methyl, and ethyl; and G is selected from the group consisting of hydrogen, oxygen, sulphur, nitrogen, phenyl and phenyl substituted with 1 to 3 substituents selected from the group consisting of amine, hydroxyl, halo, alkyl of from 1 to 4 carbon atoms and alkoxy of from 1 to 4 carbon atoms; and Z' is selected from the group consisting of hydrogen, methyl and, when G is not oxygen, sulphur or nitrogen and A is not a bond, then Z' is also selected from the group consisting of —OH, —SH, —NH$_2$, —NHR$_3$, —N(R$_3$)$_2$, —C(O)OH, —C(O)OR$_3$, —C(O)NH—NH$_2$, —C(O)NH$_2$, —C(O)NHR$_3$, —C(O)N(R$_3$)$_2$, and —OR$_4$ wherein each R$_3$ is independently alkyl of from 1 to 4 carbon atoms and R$_4$ is an alkenyl group of from 3 to 10 carbon atoms.

3. A method according to claim 2 wherein the blocking group is selected from the group consisting of sialic acid and benzyl.

4. A method for preparation of a compound of the formula IV:

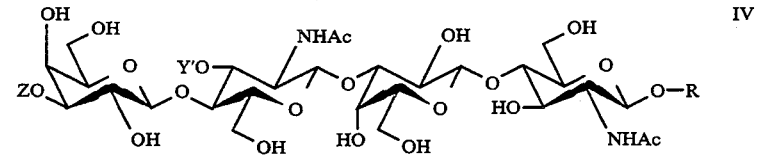

wherein R is hydrogen, a saccharide, an oligosaccharide, or an aglycon group having at least one carbon atom, Y' is L-fucose or a compatible analogue of L-fucose, and Z is sialic acid or a compatible analogue of sialic acid, which method comprises (a) sialylating a compound of the formula V

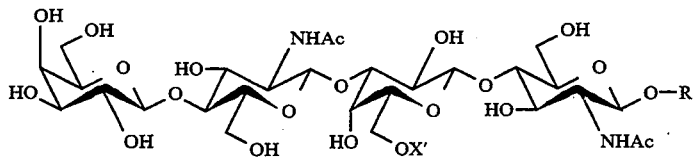

wherein R is as defined above and X' is a removable blocking group
  with a sialyltransferase in the presence of a compatible CMP derivative of sialic acid or a compatible analogue of sialic acid using an α(2-3)sialyltransferase under conditions wherein the sialic acid or analogue thereof is transferred to the 3 position of the theretofore terminal galactose unit; and
  (b) fucosylating the compound prepared in (a) above with an α(1-3)fucosyltransferase in the presence of a compatible GDP derivative of L-fucose or an analogue thereof under conditions wherein L-fucose is transferred to the 3-position of the non-reducing sugar N-acetylglucosamine unit so as to form a monofucosylated derivative of the formula VI:

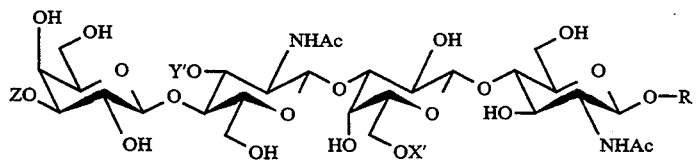

wherein X', Y' and R are as defined above; and
  (c) removing the removable blocking group from the compound formed in (b) above so as to form a compound of formula IV with the proviso that X' is not sialic acid.

5. A method according to claim 4 wherein R is selected from the group consisting of —(A)—Z' wherein A represents a bond, an alkylene group of from 2 to 10 carbon atoms, and a moiety of the form —(CH$_2$—CR$_2$G)$_n$— wherein n is an integer equal to 1 to 5; R$_2$ is selected from the group consisting of hydrogen, methyl, and ethyl; and G is selected from the group consisting of hydrogen, oxygen, sulphur, nitrogen, phenyl and phenyl substituted with 1 to 3 substituents selected from the group consisting of amine, hydroxyl, halo, alkyl of from 1 to 4 carbon atoms and alkoxy of from 1 to 4 carbon atoms; and Z' is selected from the group consisting of hydrogen, methyl and, when G is not oxygen, sulphur or nitrogen and A is not a bond, then Z' is also selected from the group consisting of —OH, —SH, —NH$_2$, —NHR$_3$, —N(R$_3$)$_2$, —C(O)OH, —C(O)OR$_3$, —C(O)NH—NH$_2$, —C(O)NH$_2$, —C(O)NHR$_3$, —C(O)N(R$_3$)$_2$, and —OR$_4$ wherein each R$_3$ is independently alkyl of from 1 to 4 carbon atoms and R$_4$ is an alkenyl group of from 3 to 10 carbon atoms.

6. A method according to claim 5 wherein the blocking group is a benzyl group.

7. The method according to claim 1 wherein fucosylation procedure (a) and sialylation procedure (c) are conducted at a temperature of from 25° to 45° C.; for a period of time of from 12 hours to 4 days; and at a pH of from about 6.5 to 7.5.

8. The method according to claim 4 wherein sialylation procedure (a) and fucosylation procedure (c) are conducted at a temperature of from 25° to 45° C.; for a period of time of from 12 hours to 4 days; and at a pH of from about 6.5 to 7.5.

9. A method for the preparation of a compound of formula I:

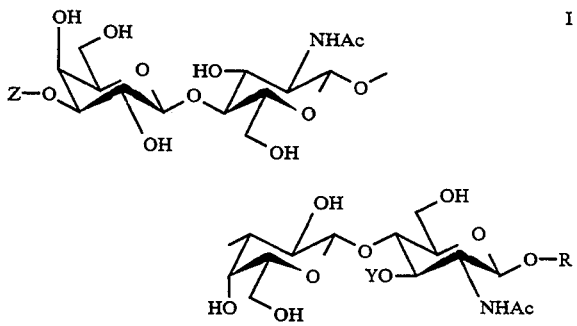

wherein R is hydrogen, a saccharide, an oligosaccharide, or an aglycon group having at least one carbon atom, Y is L-fucose or a compatible analogue of L-fucose and Z is sialic acid or a compatible analogue of sialic acid, which method comprises:
  (a) fucosylating a compound of the formula βGlcNAc(1→3)βGal(1→4)βGlcNAc-OR with an α(1-3)fucosyltransferase in the presence of a GDP derivative of L-fucose under conditions sufficient to form the compound: βGlcNAc(1→3)β-Gal(1→4)βGlcNAc-OR;
  (b) galactosylating the compound prepared in (a) above with a suitable galactosyltransferase in the presence of uridine 5' (galactopyranosyl)-diphosphate under conditions sufficient to form the compound: βGal(1→4)βGlcNAc(1→3)β-Gal(1→4)βGlcNAc-OR;
  (c) sialylating the compound formed in (b) above with a sialyltransferase in the presence of a compatible CMP derivative of sialic acid or an analogue of sialic acid using an α(2-3)sialyltransferase under conditions wherein the sialic acid or analogue thereof is transferred to the non-reducing sugar so as to form the compound of formula I above.

10. The method according to claim 9 wherein the compound of the formula βGlcNAc(1→3)β-Gal(1→4)βGlcNAc-OR is prepared by:
  galactosylating a compound of the formula GlcNAc-OR with a suitable galactosyltransferase in the presence of uridine 5' (galactopyranosyl)-diphosphate under conditions sufficient to form βGal(1→4)GlcNAc-OR; and
  N-acetylglucosaminylating the compound produced above with a suitable N-acetylglucosaminyltransferase in the presence of uridine 5' N-(acetylglucosamine)-diphosphate under conditions sufficient to form the compound βGlcNAc(1→3)β-Gal(1→4)βGlcNAc-OR.

* * * * *